United States Patent
Sharma et al.

(10) Patent No.: US 9,579,449 B2
(45) Date of Patent: Feb. 28, 2017

(54) DELIVERY SYSTEM FOR IN SITU FORMING FOAMS AND METHODS OF USING THE SAME

(71) Applicants: Upma Sharma, Somerville, MA (US); Rany Busold, Medford, MA (US); Adam Rago, Falmouth, MA (US); Gregory T. Zugates, Chelmsford, MA (US); Toby Freyman, Lexington, MA (US); Lisette Manrique Miller, Taunton, MA (US)

(72) Inventors: Upma Sharma, Somerville, MA (US); Rany Busold, Medford, MA (US); Adam Rago, Falmouth, MA (US); Gregory T. Zugates, Chelmsford, MA (US); Toby Freyman, Lexington, MA (US); Lisette Manrique Miller, Taunton, MA (US)

(73) Assignee: Arsenal Medical, Inc., Watertown, MA (US)

( * ) Notice: Subject to any disclaimer, the term of this patent is extended or adjusted under 35 U.S.C. 154(b) by 299 days.

(21) Appl. No.: 14/211,469

(22) Filed: Mar. 14, 2014

(65) Prior Publication Data
US 2014/0228745 A1    Aug. 14, 2014

Related U.S. Application Data

(63) Continuation-in-part of application No. 13/209,020, filed on Aug. 12, 2011, now Pat. No. 9,173,817, (Continued)

(51) Int. Cl.
*A61F 2/02* (2006.01)
*A61M 5/14* (2006.01)
(Continued)

(52) U.S. Cl.
CPC ..... *A61M 5/1409* (2013.01); *A61B 17/00491* (2013.01); *A61C 9/0026* (2013.01); *A61M 5/1452* (2013.01); *B01F 3/04453* (2013.01); *B01F 5/0602* (2013.01); *B01F 5/0604* (2013.01); *B01F 7/00558* (2013.01); *B01F 7/00583* (2013.01); *B01F 13/0023* (2013.01); *B01F 15/00253* (2013.01); *B01F 15/00525* (2013.01); *B01F 15/0279* (2013.01); *A61B 2017/00398* (2013.01); *A61B 2017/00495* (2013.01); *A61B 2017/00544* (2013.01); *A61B 2017/00548* (2013.01);
(Continued)

(58) Field of Classification Search
CPC ...... A61L 24/0036; A61L 27/18; A61L 27/56; A61L 27/58; A61M 5/1452; A61M 5/1409; A61C 9/0026; A61B 17/03; A61B 17/00491; A61F 2/02; A61F 2/06; A61J 1/20; A61J 1/2093
See application file for complete search history.

(56) References Cited

U.S. PATENT DOCUMENTS

2008/0161757 A1* 7/2008 Nayak ............... A61M 5/19 604/82
2011/0282381 A1* 11/2011 Cronin ............... A61B 10/0275 606/213

* cited by examiner

*Primary Examiner* — Victor Nguyen

(57) ABSTRACT

Delivery systems for in situ forming foam formulations are provided. The devices may include various actuation mechanisms and may entrain air into fluid formulation components in a variety of ways, including mixing with air and the addition of compressed gas.

11 Claims, 35 Drawing Sheets

Related U.S. Application Data which is a continuation-in-part of application No. 12/862,362, filed on Aug. 24, 2010.

(60) Provisional application No. 61/852,051, filed on Mar. 15, 2013.

(51) Int. Cl.

| | |
|---|---|
| *A61B 17/00* | (2006.01) |
| *B01F 5/06* | (2006.01) |
| *B01F 7/00* | (2006.01) |
| *B01F 13/00* | (2006.01) |
| *B01F 15/00* | (2006.01) |
| *B01F 15/02* | (2006.01) |
| *B01F 3/04* | (2006.01) |
| *A61C 9/00* | (2006.01) |
| *A61M 5/145* | (2006.01) |
| *A61M 5/19* | (2006.01) |
| *B05C 17/005* | (2006.01) |
| *B65D 81/32* | (2006.01) |
| *A61B 17/88* | (2006.01) |
| *A61M 13/00* | (2006.01) |

(52) U.S. Cl.
CPC ........ *A61B 2017/8838* (2013.01); *A61M 5/19* (2013.01); *A61M 13/003* (2013.01); *A61M 2205/103* (2013.01); *B05C 17/00553* (2013.01); *B65D 81/325* (2013.01)

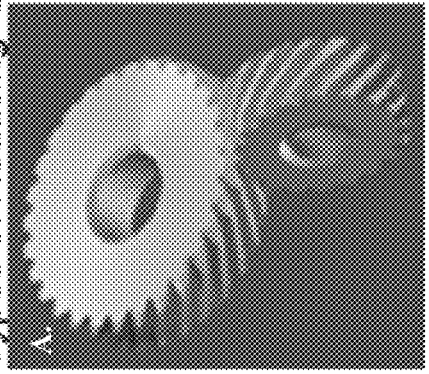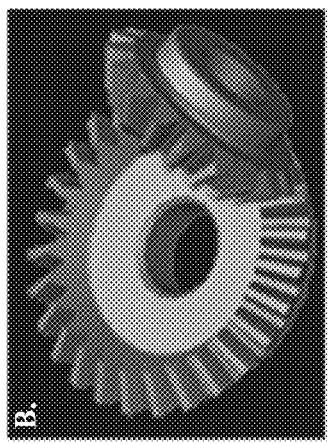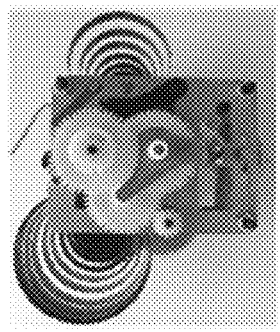
Figure 21.
Figure 22.

DELIVERY SYSTEM FOR IN SITU FORMING FOAMS AND METHODS OF USING THE SAME

CROSS-REFERENCE TO RELATED APPLICATIONS

This application claims priority to U.S. Application Ser. No. 61/852,051 filed Mar. 15, 2013 entitled "Delivery System for In Situ Forming Foams and Methods of Using the Same," and further claims priority to U.S. application Ser. No. 13/209,020 filed Aug. 12, 2011 entitled "In Situ Forming Hemostatic Foam Implants," which in turn is a continuation-in-part of U.S. application Ser. No. 12/862,362 filed Aug. 24, 2010 entitled "Systems and Methods Relating to Polymer Foams." The entire disclosure of each of the foregoing applications is hereby incorporated by reference for all purposes.

STATEMENT OF GOVERNMENT SUPPORT

This invention was made with Government support under award nos. W911NF-10-C-0089 and W911NF-12-C-0066 awarded by the Defense Advanced Research Projects Agency (DARPA). The Government has certain rights in the invention.

TECHNICAL FIELD

The present invention relates to medical devices for the delivery of in situ forming foams to patients.

BACKGROUND

In situ forming polymer foams, such as the Arsenal Foam Technology commercialized by Arsenal Medical (Watertown, Mass.), have a number of important biomedical applications, including the prevention or treatment of hemorrhage, particularly from non-compressible or difficult-to-visualize wounds, vascular embolization, arteriovenous malformation, AV fistulas, space filling and bulking (e.g. following surgical resection, or for cosmetic purposes), prevention of tissue adhesion, hernia repair, prevention or treatment of reflux, and temporary or permanent occlusion of body lumens for a variety of applications including sterilization, prevention of calculus migration during lithotripsy, and other applications. The diversity of applications for in situ forming foams reflects significant advantages possessed by such foams relative to existing technology, including, without limitation their incorporation of well characterized, biocompatible materials; the ability to deliver in situ forming foams to closed cavities, for example intravascularly; the ability to deliver in situ forming foams to difficult-to-access body sites; the ability of in situ forming foams to expand into empty space or into space filled with blood, and the ability of the foam to fill a body cavity.

In situ forming foams are typically generated by delivering and mixing multiple liquid-phase components (such as a polyol component and an isocyanate component, which form a polyurethane foam). Each such liquid-phase component may comprise multiple different materials or agents that determine the mechanical properties of the foam and/or the kinetics of foam formation. Pores within the foam may be formed by a blowing reaction and/or by the entrainment of gas before or during foam formation. While blowing agents are effective to drive the foaming and expansion of in-situ forming foams, blowing agents or their byproducts may be toxic, and entrained gas may be preferred for applications in which such toxicity is preferably avoided.

In situ forming foams are particularly well suited to treating injuries in challenging settings such as in remote settings, and on the battlefield. However, in spite of their advantages, in situ forming foams have not been widely used because of the technical challenges associated with developing suitable in-situ foaming formulations for different applications and delivering such formulations to specific anatomical sites. Additionally, to maximize their efficacy in challenging settings such as on the battlefield, delivery systems for in situ forming foams should preferably be easy to assemble, provide a safe way to access the target site in the body, have a minimal number of parts, and rapidly aerate, mix, and deliver volumes of approximately 80-200 mL of in situ foaming formulations to patients. While low-viscosity materials can be aerated by simple shaking, gas entrainment poses a significant challenge in higher viscosity formulations, which may be necessary to generate foams having desirable physical and therapeutic characteristics.

There is, accordingly, a need in the art for delivery systems for efficiently delivering viscous gas-entrained in situ forming foam formulations to sites of interest in patients' bodies in non-clinical settings such as on the battlefield.

BRIEF DESCRIPTION OF THE INVENTION

The present invention addresses the need described above by providing, in one aspect, a medical device for the delivery of in situ forming foams to sites on or within the body. The medical device includes a fluid cartridge that includes multiple fluid chambers and multiple pistons, and the volume of each fluid chamber is determined by the position of a piston. At least one chamber includes an impeller, and the device also includes an actuator to move the impeller and/or the piston, as well as a static mixer that connects to each of the chambers. The actuator may connect to a piston so it moves the piston in the chamber, and the actuator can be any of a squeeze handle, crank, ratchet, or piston pump. Moving the actuator once may be sufficient to eject substantially all of the contents of a chamber, or the actuator may need to be moved multiple times. The device can also include a gas cylinder or a motor. The impeller is optionally solid or porous and contacts the wall of the chamber. The static mixer can include a cylindrical outer shell with a tapered end that has multiple apertures, plus a lumen defined by the outer shell which contains multiple mixing elements. The mixing elements can be X-grids, beads, or mesh. The medical device is also optionally mechanically driven such that no electrical or pneumatic parts are used.

In another aspect, the invention relates to methods for treating patients that include the steps of providing an activatable delivery device loaded with multiple liquid-phase foam forming components, and activating the delivery device to aerate at least one liquid phase component, then mixing the components to form a gas-entrained foaming composition and dispensing the composition into a patient's body cavity. The method optionally includes one or more of the following: the delivery device can include a selector for selecting the quantity of foaming composition to be delivered to the patient, and the method can include using the selector to select such a quantity; activating the delivery device can comprise actuating a trigger connected to a fluid impeller that mixes or aerates the components, and activating the trigger can also cause the ejection of the gas-entrained foaming composition from the delivery device; the trigger can be actuated by squeezing, and the delivery device can also include a lockout to prevent ejection of the foaming composition prior to aeration of at least one liquid phase component. The delivery device can also include a tip that can be inserted into a patient, and the method can include putting a dilator sheath into a body wall of the patient and inserting the tip into the patient through the dilator sheath. The tip can include a static mixer, and when the trigger is actuated, the liquid phase components can be forced across the static mixer and out of the tip of the delivery device into the patient.

In yet another aspect, the invention relates to methods for entraining gas into the formulation prior to delivery into the body.

In another aspect, the invention relates to a lock out mechanism and a ready indicator to prevent a user of a medical device according to the invention from administering un-aerated formulations to patients.

In still another aspect, the invention relates to a method of mixing the two part formulation after air entrainment and prior to the dispensing into the body.

DESCRIPTION OF THE DRAWINGS

In the drawings, like reference characters refer to like features throughout the various figures. The figures provided herein are not necessarily drawn to scale, with emphasis being placed on illustration of the principles of the invention.

FIGS. 21A-C include depictions of exemplary reducing gears compatible with certain embodiments of the invention.

FIG. 22 includes a depiction of an exemplary reducing gear compatible with certain embodiments of the invention.

DETAILED DESCRIPTION OF THE PREFERRED EMBODIMENTS

The inventors have created an in situ forming foam to treat severe abdominal, junctional and/or pelvic hemorrhage that can be administered by injecting and mixing together two liquid phases, triggering a chemical reaction which causes foaming material to expand and distribute throughout the abdominal cavity. Administration of this foam has been shown to provide a significant survival advantage in a model of severe abdominal hemorrhage in swine. However, translation of this technology into a successful product requires development of delivery system to enable effective administration of foams to treat injuries, and it would be highly desirable for such a system to be functional outside of the hospital setting, for example on the battlefield in a far-forward environment. A successful delivery device is preferably characterized by the following: (a) compatibility with a safe and simple method to gain entry into the desired body cavity, (b) easy assembly with minimal number of components, (c) rapid delivery of the formulation, (d) delivery of the appropriate volume of the liquid phases (80-200 mL), (e) successful mixing of the two liquid phases, (f) a method to easily entrain air into one of the phases, (g) prevention of deployment of unaerated formulation, (h) appropriate distribution of the liquid phases in the cranial, caudal, and lateral directions, (i) ability to select the appropriate dose, if required, and (j) biocompatible materials. Disclosed herein are systems and components that can achieve all or part of the above requirements.

Ratchet Mechanism

Figure 1:
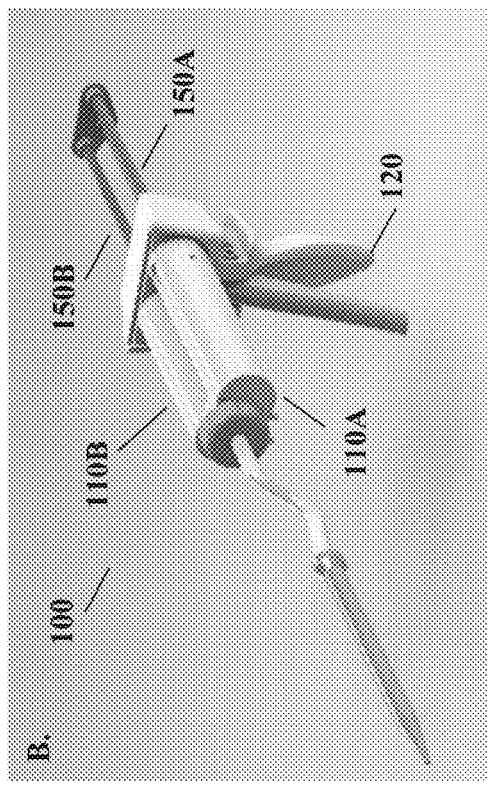
FIGS. 1A-B include schematic depictions of a delivery system according to certain embodiments of the invention.
Figure 1:
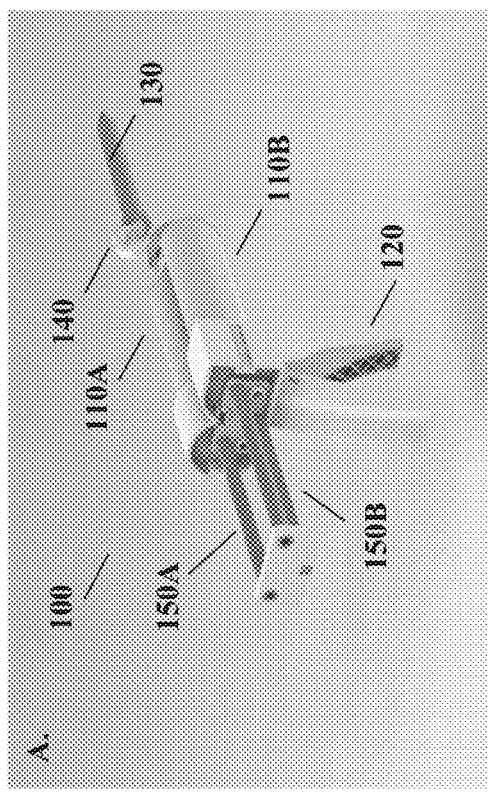
Figure 2:
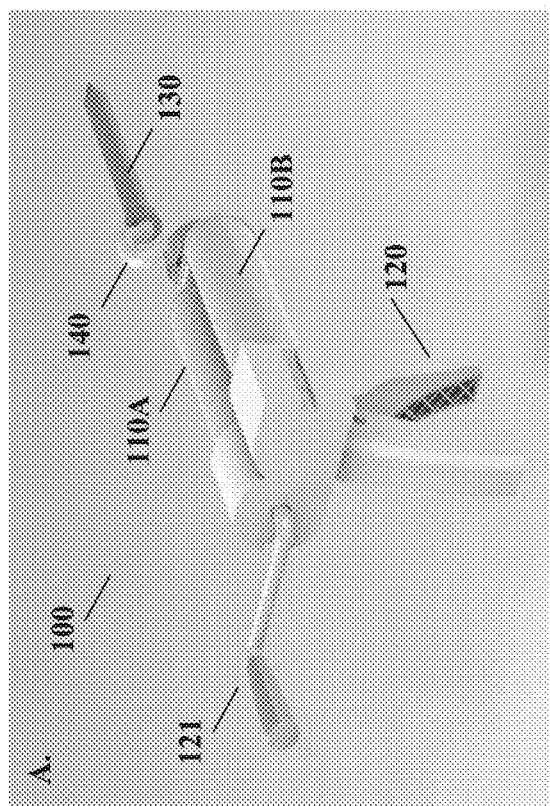
FIGS. 2A-B include schematic depictions of a delivery system according to certain embodiments of the invention.
Figure 3:
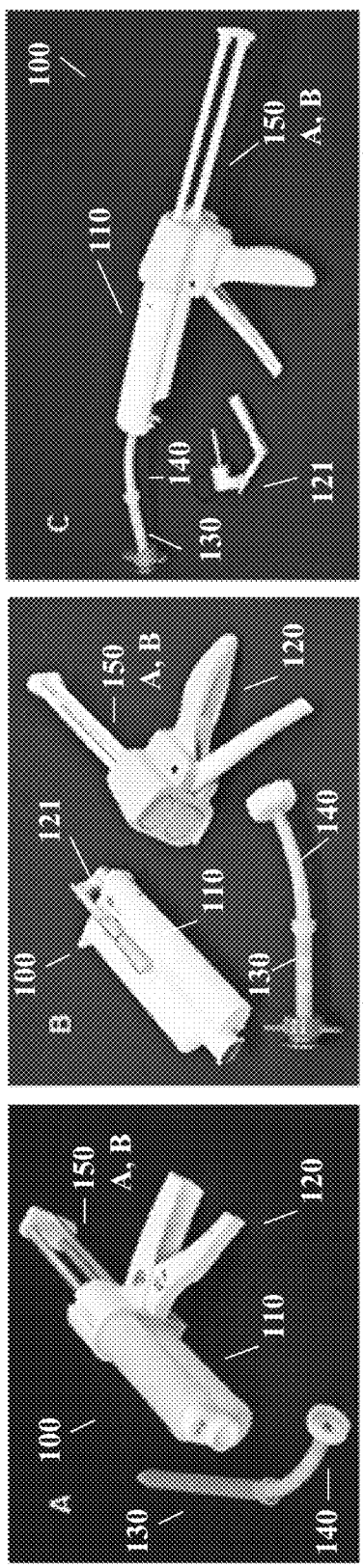
FIGS. 3A-C include multiple views of partially disassembled delivery systems according to the invention.
Figure 4:
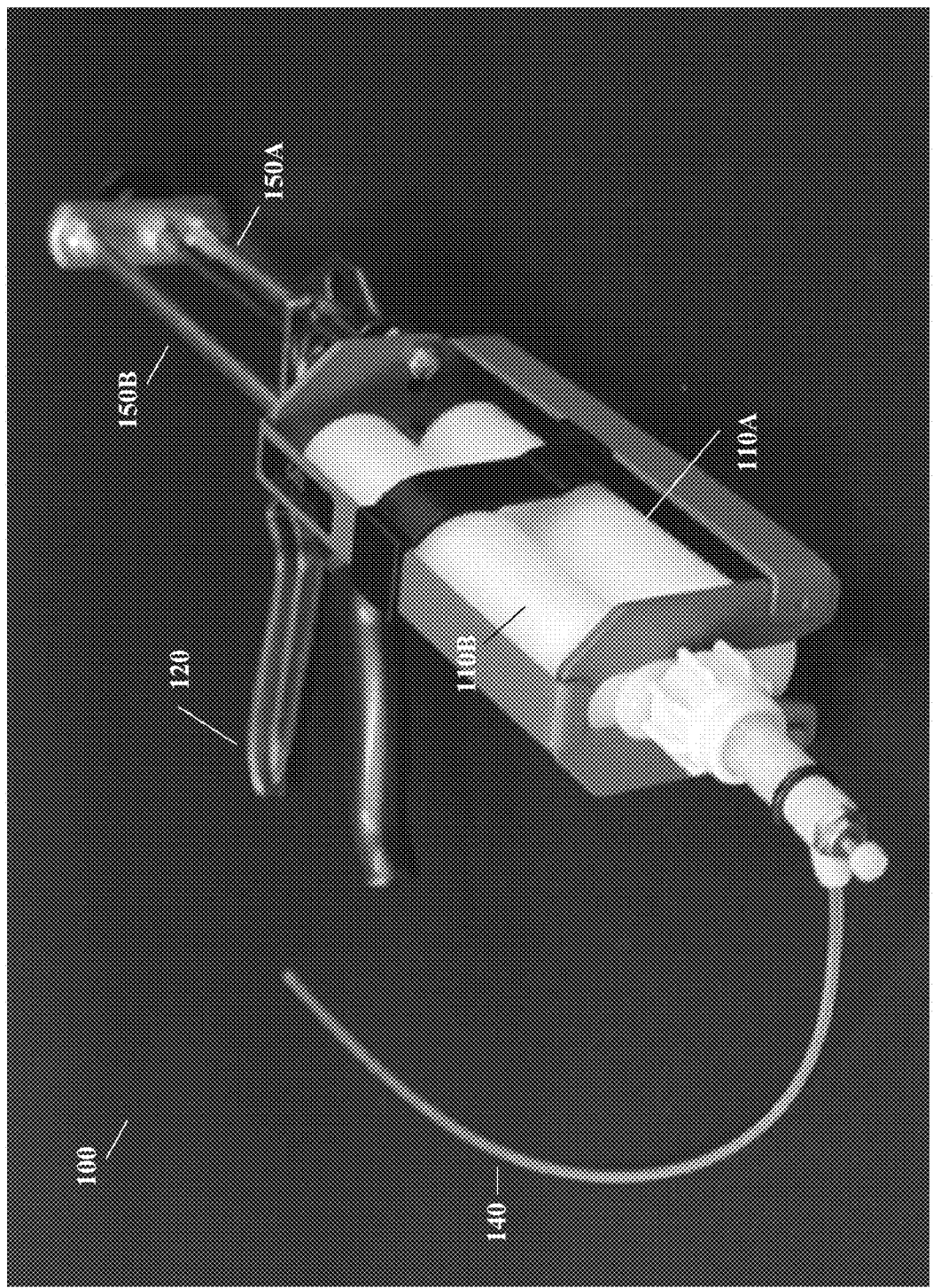
FIG. 4 includes a view of a delivery system according to certain embodiments of the invention.

An exemplary delivery system 100 according to certain embodiments of the invention includes a dual barrel cartridge 110 comprising two adjacent fluid chambers, each chamber configured to hold one of the liquid phases A and B. The delivery system 100 also includes a squeezable grip 120, a static mixing nozzle 130 with a flexible connector 140, and piston push rods 150A, B for urging the liquid phases from each of the barrels 110A, B of the cartridge 110. This design can have two variants: (1) a single actuation mechanism 120 (e.g. a squeeze handle) effectuates both air entrainment and formulation deployment, as illustrated in FIG. 1; or (2) two independent actuation mechanisms 120, 121, one for air entrainment (e.g. a crank handle) and a separate one (e.g. a squeeze handle) for deployment, are built into the design, as shown in FIG. 2. As the grip 120 is squeezed, it engages the piston push rods 150A, B, through the use, for example, of two friction plate and springs and ratchets the rod forward thereby deploying the material. Other means for engaging the push rods include toothed surfaces, pulleys, and lead screws. A form factor prototype was created, as shown in FIG. 3, to understand ergonomics of the device and a functional prototype, depicted in FIG. 4, was successfully used to deploy in situ forming formulations.

Preferred embodiments of the invention incorporate mechanisms to prevent the deployment of unaerated or partially aerated formulations, which mechanisms are optionally coupled to an indicator that indicates to a user that the formulation is fully aerated and ready for deployment. Additionally, preferred embodiments of the invention allow users to select a quantity of aerated formulation that will be delivered to the patient. These aspects of the invention are described more fully below.

Aeration Mechanism

Figure 5:
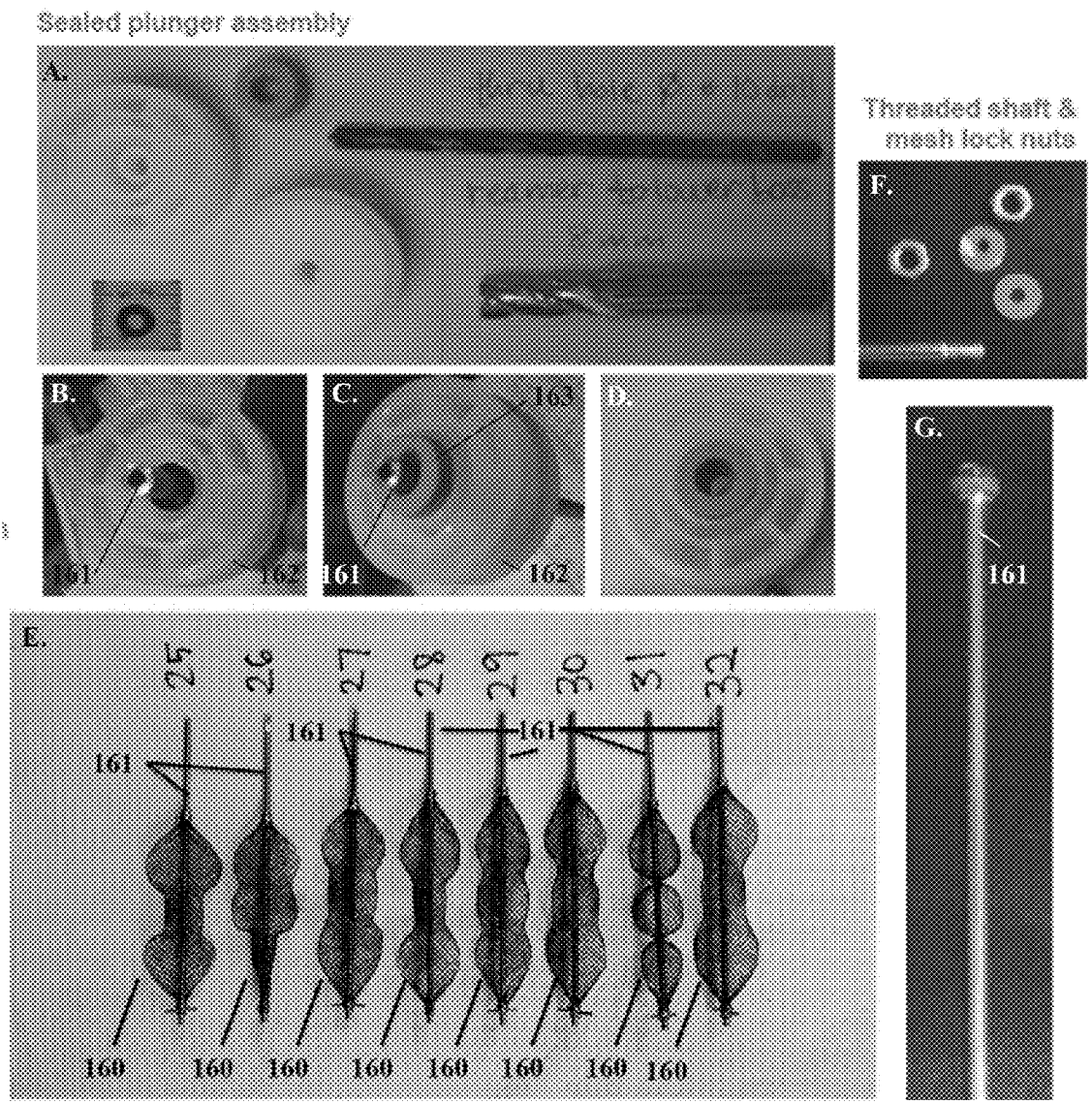
FIGS. 5A-G include multiple views of seal plunger assemblies and helical mesh assemblies according to certain embodiments of the invention.

Air entrainment in one of the liquid phases may be required to create a foam with the desired properties. Generally, at least one fluid chamber of the cartridge will include both a liquid phase and a gas portion (termed a "head") that is mechanically mixed into the liquid phase in order to yield a gas-entrained liquid phase. In certain embodiments, entrainment is accomplished through the use of a helical or zig-zag mesh assembly 160 within at least one of the fluid barrels 110A or B. Meshes useful in embodiments of the invention are made of any suitable material, including metals (e.g. stainless steel, nitinol) or polymers (e.g. polypropylene). An exemplary helical mesh is shown, at various angles of rotation, in FIG. 5E. The mesh is formed of a shape memory material, preferably nitinol, which is flexible but resilient enough to resist tearing when used to aerate viscous formulations. The mesh 160 is generally planar, and moves through a plurality of turns along the length of a rod 161. The mesh 160 is also slideably attached to the rod 161 so that, as the plunger is advanced through the chamber, the mesh collapses. The mesh 160 fits within the barrel 110A, B such that the mesh 160 makes contact with the wall of the barrel. Though not wishing to be bound by theory, it is believed that contact between the mesh and the barrel improves the efficiency of air entrainment, as it is believed that such contact prevents air bubbles from moving around the mesh and along the wall, instead forcing such bubbles to remain in contact the mesh as the mesh moves within the liquid phase.

The cartridge 110 is sealed at the end with a plunger 162, which in turn includes a through lumen for the rod assembly 161 so that the helical mesh can rotate. O-rings 163 are used as seals to prevent leakage from the plunger through the lumen. The cartridge 110 is held by the user at an angle Θ between 0 (vertical) and 90 (horizontal) degrees, preferably between 45 and 90 degrees and the helical mesh assembly 160 is rotated to entrain air into the liquid phase within the barrel 110A, B. Angle Θ is selected in order to promote the incorporation of a head of air present in at least one barrel of the cartridge 110 into the liquid phase: holding the cartridge in a 45 to 90 degree position relative to vertical (i.e. horizontally or near-horizontally) helps to distribute the head of air along the barrel of the cartridge and aid in easily entraining the air using the mesh mixer. Once air entrainment is completed, the plunger 162 is advanced forward by the piston push rods and the helical mesh assembly 160 folds like an accordion or simply compresses down to a low profile to permit dispensing of all or substantially all (i.e. greater than 90%) of the contents of the barrel 110A, B.

Site Access Method

Delivery systems of the invention can be used in conjunction with site access devices to permit deployment of in situ forming foams into closed cavities, such as the abdominal cavity in cases of internal bleeding, including one or more of the following: abdominal bleeding, junctional/inguinal bleeding, and pelvic bleeding. An exemplary procedure to obtain access to the abdominal cavity and insert the delivery system nozzle into the body will include a skin incision and introduction of an entry port into the abdomen directly above the umbilicus. The entry port can range from 1.8 mm to 13 mm ID. The delivery nozzle will be placed into the entry port thereby providing a pathway for the material into the cavity. Detailed steps of this exemplary procedure include the following:

(1) Perform a small skin nick with a scalpel above the umbilicus
(2) Insert entry port (such as a Veress needle with dilator sheath) to abdominal cavity
(3) Remove at least a portion of the entry port (e.g. the Veress needle may be retracted, leaving the dilator sheath in place within the patient), and dispense lubrication (polyol or similar) into sheath if required.
(4) Hold dilating sheath stable in one hand and insert the delivery system nozzle into the sheath with the other hand.
(5) Advance the nozzle into the abdomen using a slow rocking motion. An optional positive stop on the delivery nozzle indicates that the nozzle is in the correct location.
(6) Attach nozzle to the delivery system and dispense material.

Figure 6:
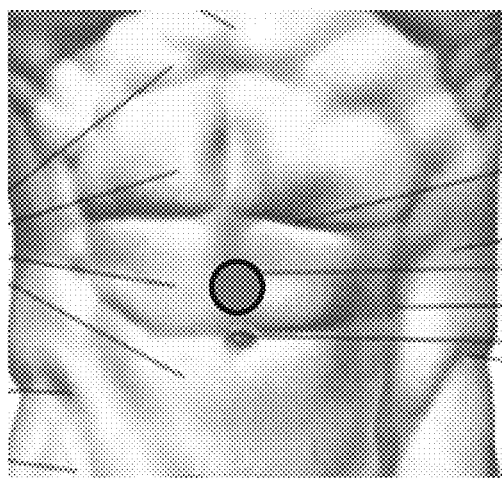
FIG. 6 includes a schematic depiction of an exemplary site for a skin incision to access the abdominal cavity of a patient according to certain embodiments of the invention.
Figure 7:
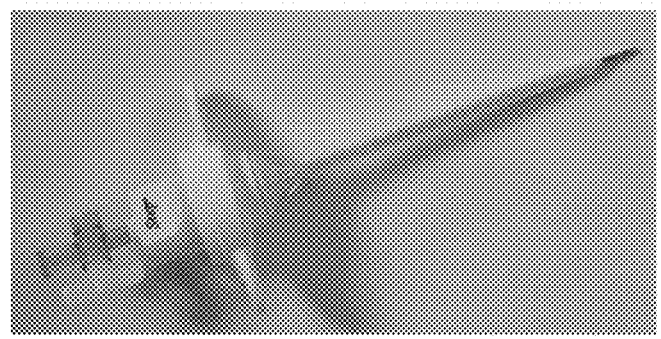
FIG. 7 includes a view of a Veress needle with a Dilator Sheath.
Figure 8:
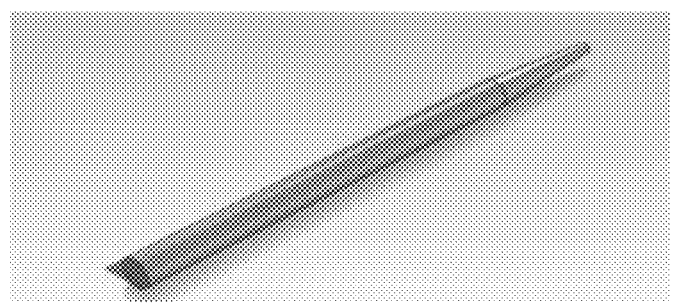
FIG. 8 includes a schematic view of a dilating nozzle according to certain embodiments of the invention.

Devices that may be useful for obtaining access to closed cavities such as the abdominal cavity include, without limitation, a 6 cm Veress needle as shown in FIG. 6; a short (e.g. about 5 cm) dilating sheath as illustrated in FIG. 7; or an 11 mm diameter nozzle with a long taper (e.g. about 4.4 cm), as shown in FIG. 8.

Static Mixer

Figure 9:
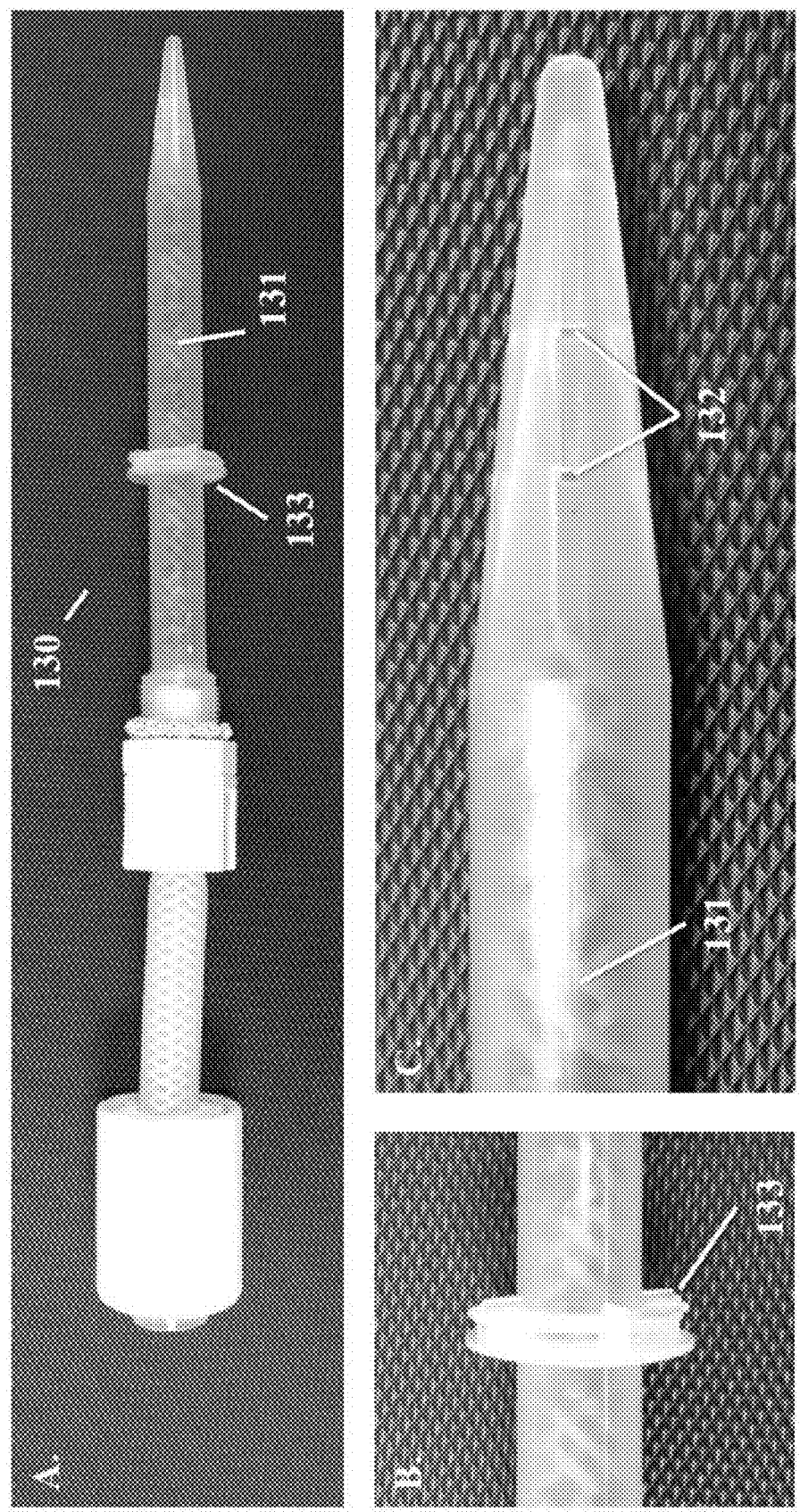
FIGS. 9A-B include multiple views of static mixing tips according to certain embodiments of the invention.
Figure 10:
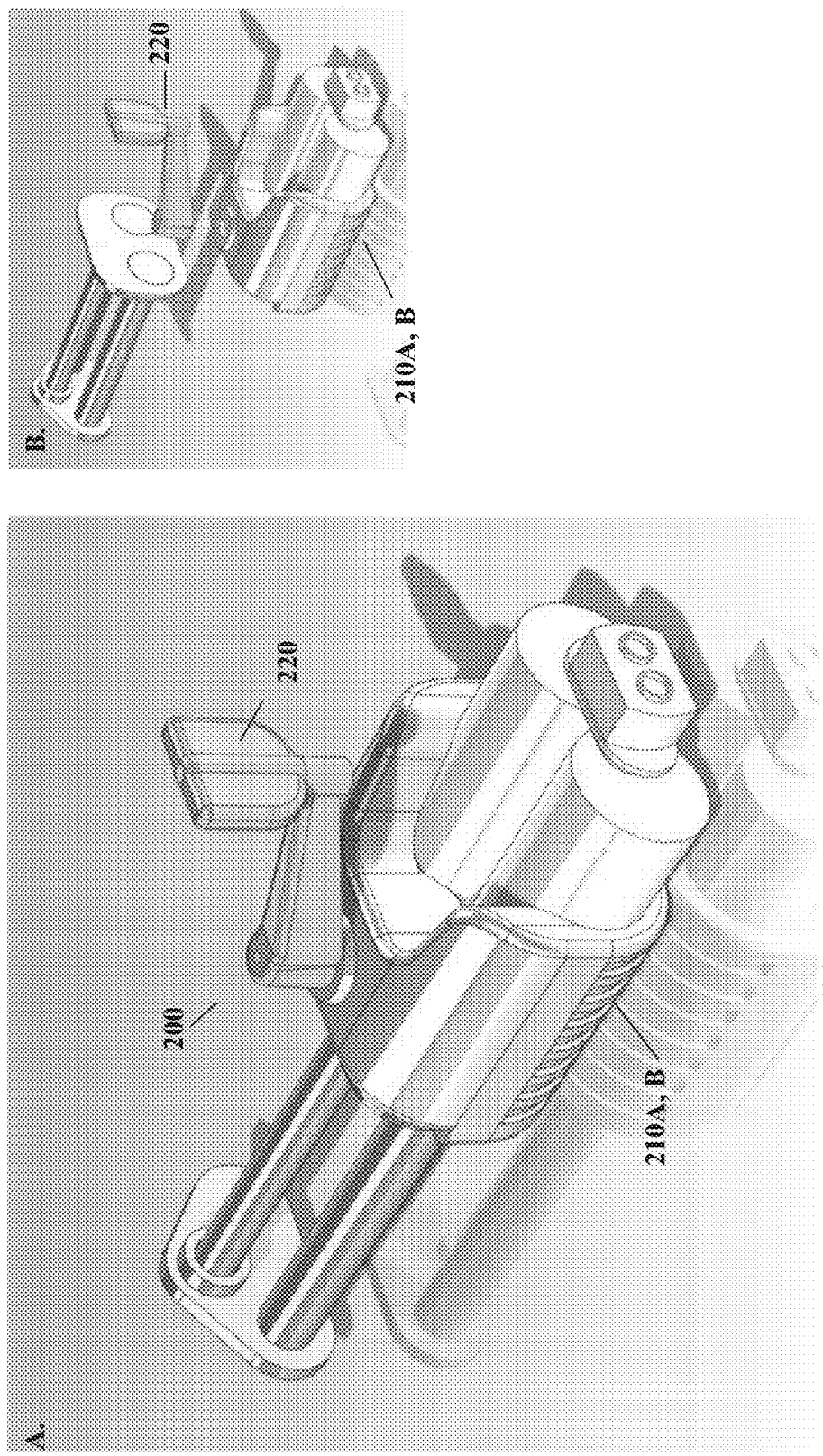
FIGS. 10A-B include schematic depictions of a delivery system according to certain embodiments of the invention.

In certain embodiments, a static mixer 130 is used to mix the two liquid phases—which in some cases are characterized by different viscosities and/or densities, and may be challenging to mix together—prior to their deposition in the abdominal cavity. An exemplary static mixer 130 as shown in FIG. 9 consists of a plurality of stacked X-grid elements 131; in the nozzle of FIG. 9, the X-grid elements 131 are stacked at 90 degree angles relative to adjacent elements. The X-grid elements 131 advantageously promote mixing at the outer walls of the nozzle and have been used successfully to mix viscous urethanes, adhesives and foam systems in other settings. Though X-grid elements are preferred, other mixing means are within the scope of the invention, including static means such as beads, mesh, and patterned static mixer elements having other shapes, such as helical, quadro, etc., as well as dynamic mixing elements as are known in the art. The mixer 130 can include a plurality of dispensing apertures 132 at its tip, to permit dispersion of gas-entrained, mixed in situ forming formulations in multiple directions within the body of the patient. For example, the mixer 130 depicted in FIG. 9 includes several dispensing apertures 132 at its dip, for dispensing formulations in multiple directions. In other embodiments, the apertures are distributed evenly around the circumference of the nozzle to allow for placement into the body without specifically orientating it in a direction. To ensure that the static mixer 130 is inserted within the patient to a useful length—into the body cavity being filled, but not far enough to contact the wall of that tissue—the mixer optionally includes a stop 133 disposed on the outer surface of the static mixer 130 at a useful distance from the tip of the mixer 130. In some cases, the stop 133 is sized and shaped to interlock with a portion of the dilator sheath or other tool used to access the body cavity, thereby providing a user with a positive indication that the tip of the static mixer 130 is positioned appropriately for the delivery of foam to the body cavity.

Devices according to the embodiments described above advantageously provide for the mixing, aeration, distribution, and injection of foam for treatment of incompressible wounds. These devices have a number of important qualities: they utilize simple, familiar mechanisms for aeration and injection (turning a crank and/or squeezing a ratchet), simplifying use in challenging settings such as in combat. They do not require power or compressed gas, which may lead to failures or safety hazards on the battlefield. Additionally, devices according to the embodiments described above have small numbers of pieces provided to the user (5 or less) and can be assembled quickly. The air entrainment mechanisms described above allow for quick and even distribution of air into liquid components prior to their deployment. Each step (assembly, site insertion, aeration, dispense) can be performed quickly and safely in a battlefield environment. However, alternate embodiments utilizing different elements and potentially having different characteristics than those described above are also within the scope of the invention, and are described in greater detail below.

External Lead Screw

Figure 11:
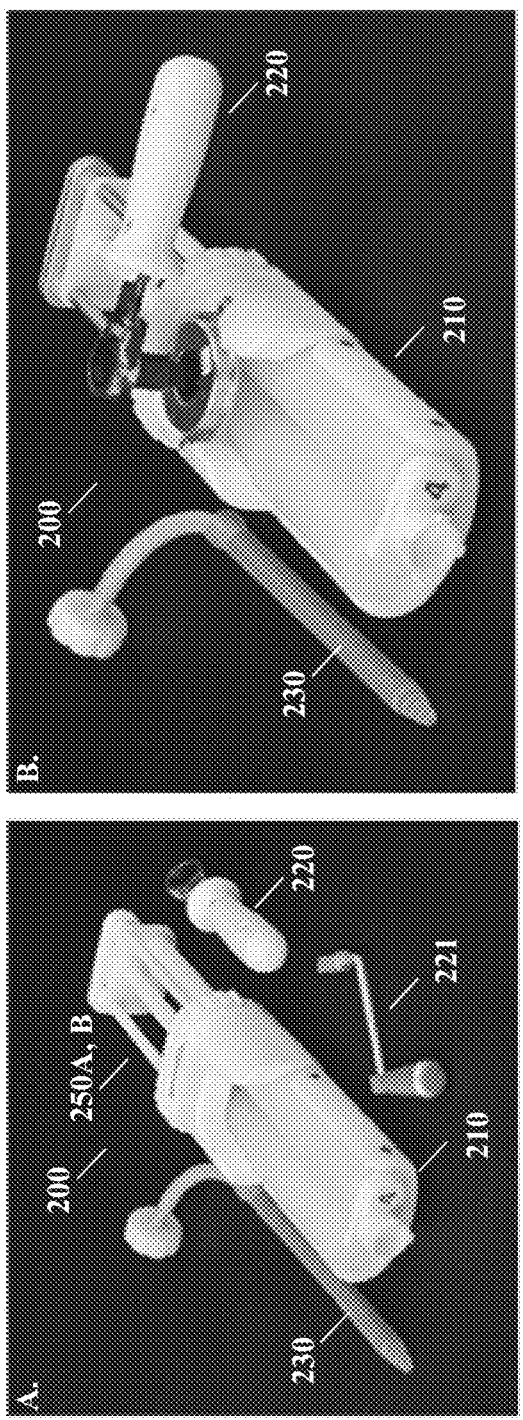
FIGS. 11A-B include views and a schematic depiction of a delivery system according to certain embodiments of the invention.

In an exemplary delivery system 200 according to certain alternate embodiments, a lead screw 280 is used to translate motion of the actuation mechanism 220 to advance the piston push rods 250A, B, thereby urging liquids contained in a dual barrel cartridge 210A, B out of the cartridge 210 and through a static mixer 230. The lead screw 280 can be advanced using any suitable actuation mechanism 220, including without limitation a crank, ratchet, or socket wrench. Delivery systems 200 according to this embodiment are characterized by an advantageously simple design, and accordingly simple steps for use, as a single mechanism is used to both entrain air and deploy the liquids. For example, in the unassembled state, the user can take the crank handle (shown in green) place it at the rear of the device and aerate the foam. The user can then remove the crank handle, assemble the lead screw, reposition the crank at the top of the device (as depicted in the assembled drawing) and deploy the liquids by turning the crank. FIG. 11 depicts actual prototypes using a socket wrench as an actuation mechanism.

Internal Pulley

Figure 12:
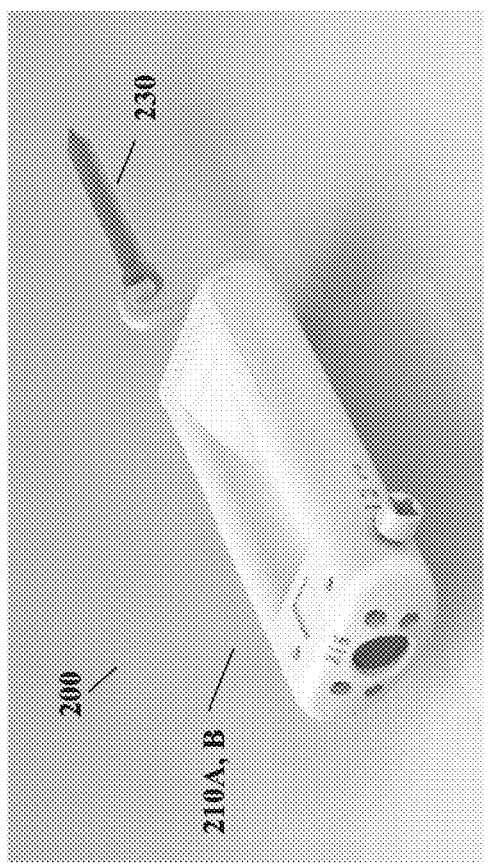
FIG. 12 includes a schematic depiction of a delivery system according to certain embodiments of the invention.
Figure 13:
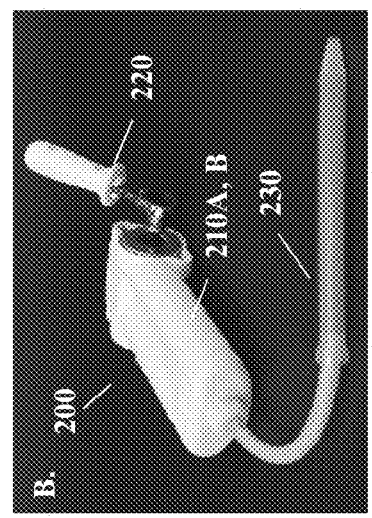
FIGS. 13A-B include views of a delivery system according to certain embodiments of the invention.
Figure 13:
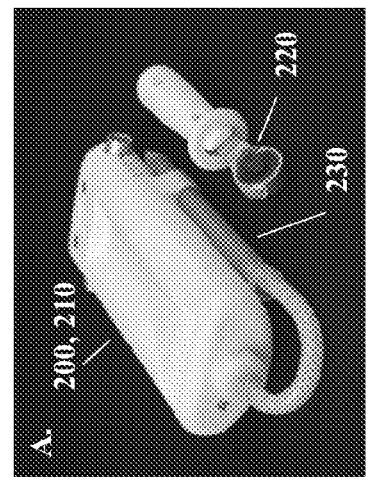

In certain embodiments, a pulley mechanism is used as an actuation device 220, 221 for either advancing the piston push rods 250 and/or to entrain air into one or more liquid phases within the dual barrel assembly 210. As illustrated in FIG. 12 the pulleys are internal to a single unit which enables low cube volume and easy packability. Another advantage of this prototype is that a single method of actuation can be used for both aeration and deployment. As an example, and as shown in FIGS. 12 and 13, a socket wrench can be rotated to aerate the fluid; after aeration is complete, a pop-out indicator button in the back end of the system moves from a first position to a second position, indicating a change over from aeration to deployment. The pop-out indicator button is driven by a counter mechanism as described in more detail below. The indicator button, once it has moved into the second position the button can be depressed in order to configure the delivery system to dispense the liquid phases from the cartridge. Continuing to rotate the socket wrench urges the aerated liquid phase or phases through the mixing tip and into the body.

Piston Pump

Figure 14:
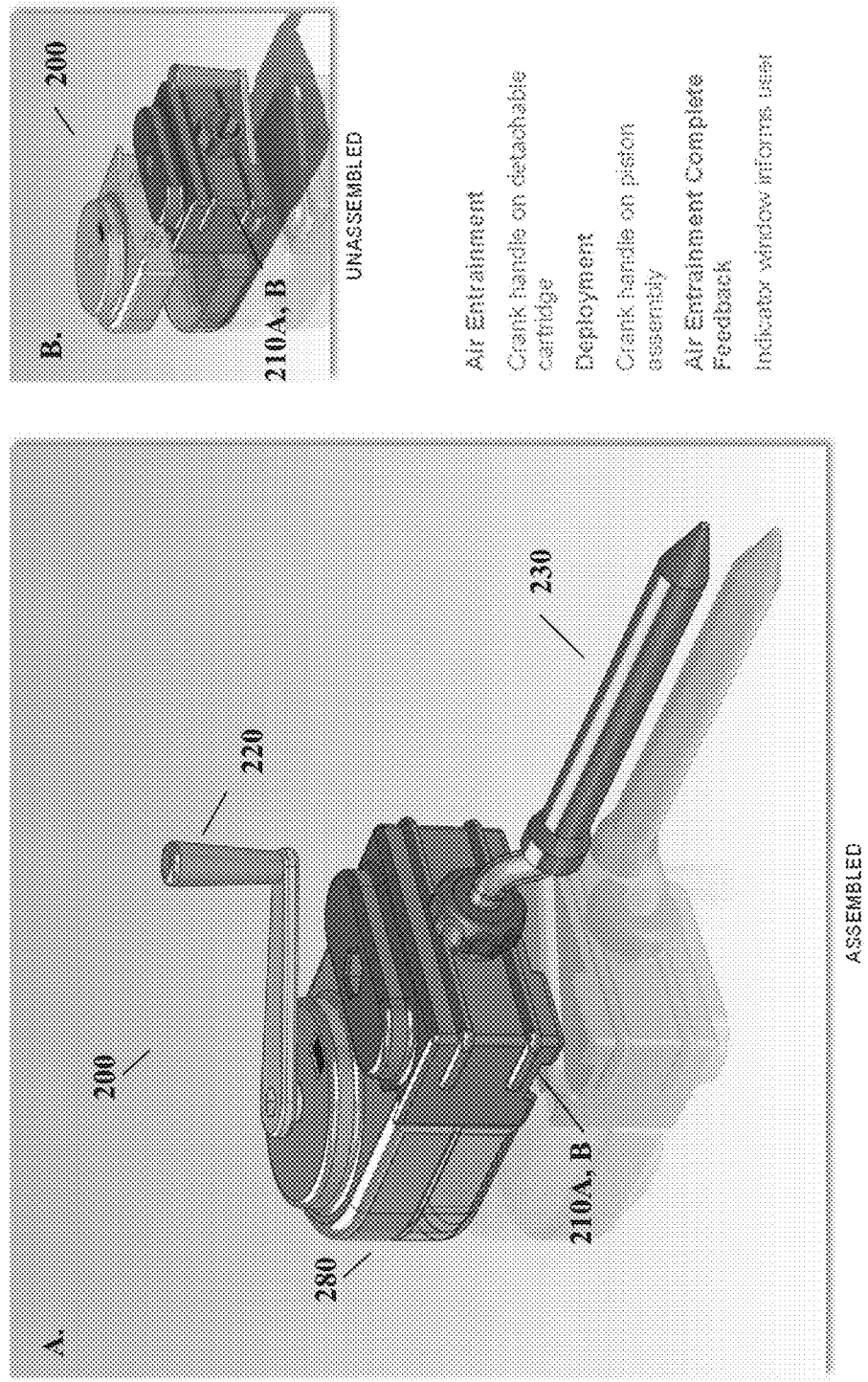
FIGS. 14A-B include schematic depictions of a delivery system according to certain embodiments of the invention.
Figure 15:
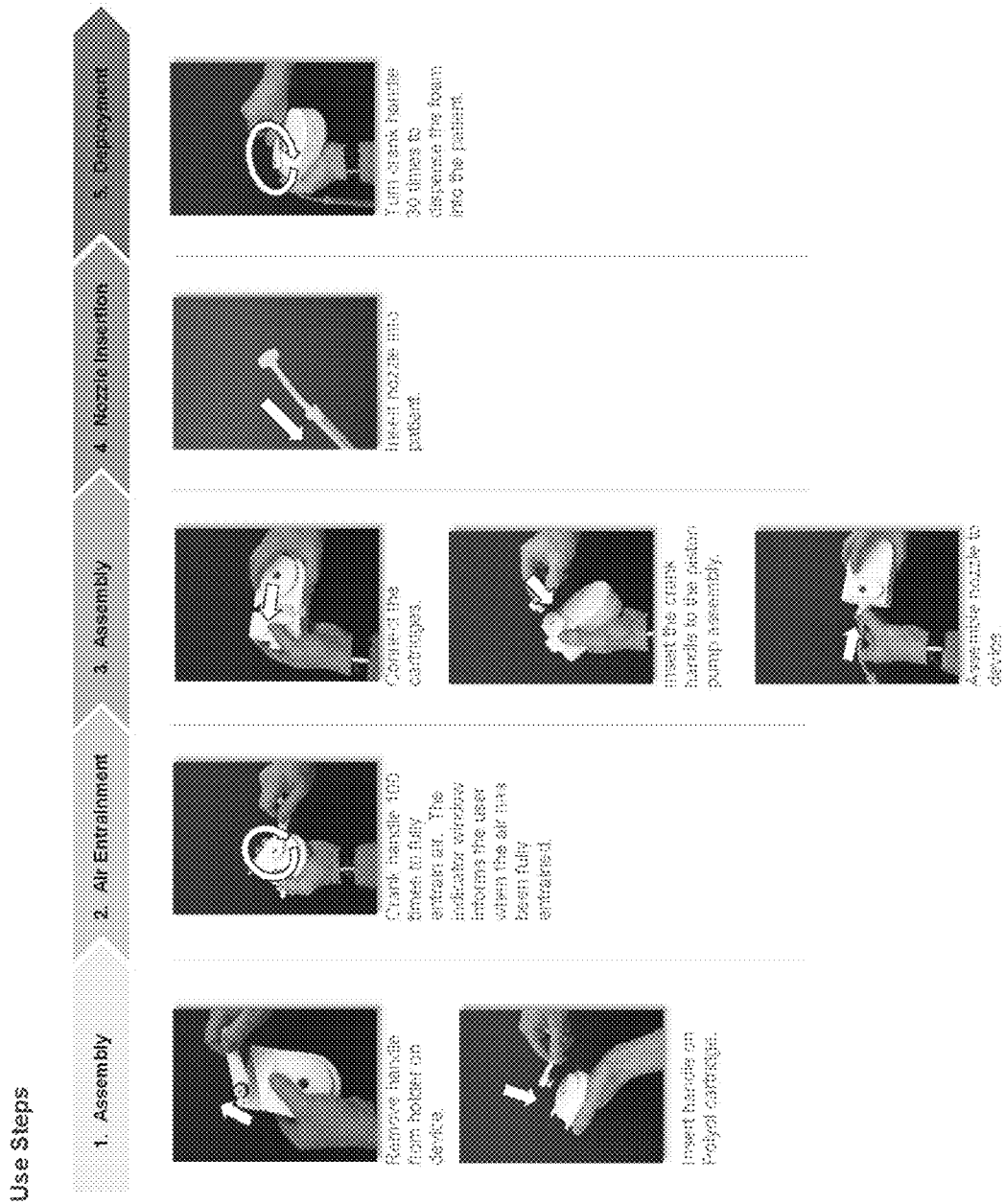
FIG. 15 includes a depiction of the steps of using a delivery system according to certain embodiments of the invention.

Devices according to certain embodiments may utilize a diaphragm pump 280 to expel the fluids into the mixing nozzle and deploy the formulation into the body. In an exemplary embodiment, shown in FIGS. 14 and 15, an unassembled device comes in three major pieces: a cartridge containing a polyol liquid phase, a cartridge containing an isocyanate liquid phase, and a diaphragm pump with a nested handle. As shown in steps 1 and 2 of FIG. 15, the nested handle is removed from the diaphragm pump and inserted into the polyol cartridge. The handle is rotated to entrain air into the polyol liquid phase. Once aeration is completed, the crank can be removed and the isocynanate and polyol cartridges can be attached to the diaphragm pump (as shown in step 3 of FIG. 15). The crank is then attached to the diaphragm pump and used to deploy the liquid phases in the cartridges. As the diaphragm moves from side to side it draws small amounts of polyol, then isocyante and pushes them into the flexible tube and through the mixing nozzle. The diaphragm pump creates alternating flows of isocyanate and polyol that are mixed in the nozzle instead of injecting two side by side streams of polyol and isocyanate. A dynamic mixer may provide more efficient mixing when a diaphragm pump dispensing mechanism is used.

Aeration Mechanism

Figure 16:
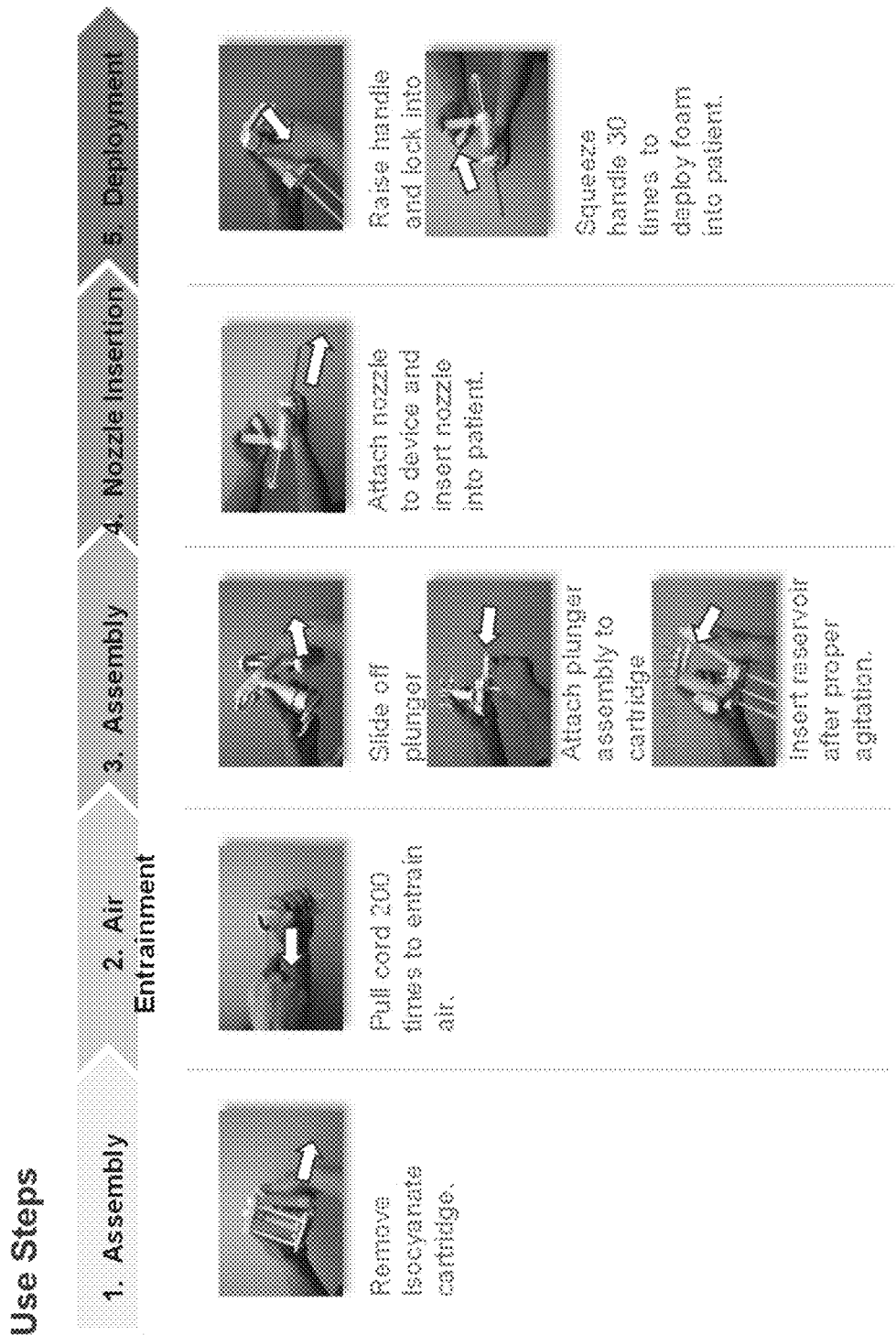
FIG. 16 includes schematic depictions and a photograph of delivery systems according to certain embodiments of the invention.
Figure 17:
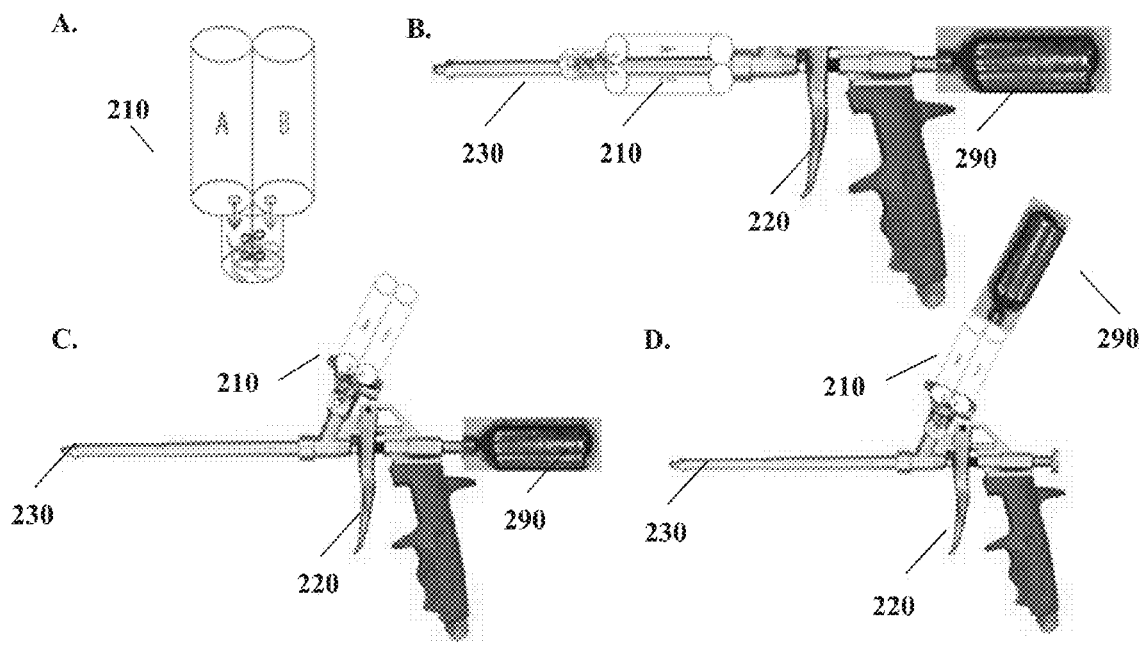
FIGS. 17A-D include schematic depictions and a photograph of delivery systems according to certain embodiments of the invention.
Figure 18:
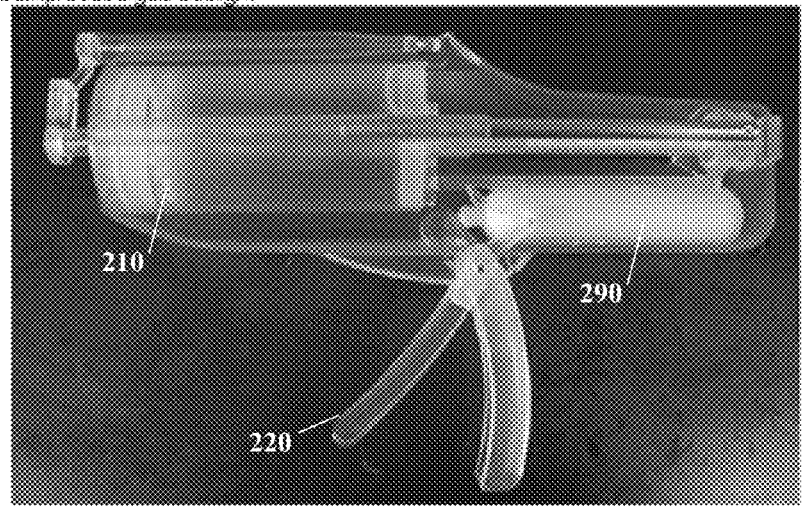
FIG. 18 includes schematic depictions and a photograph of delivery systems according to certain embodiments of the invention.
Figure 19:
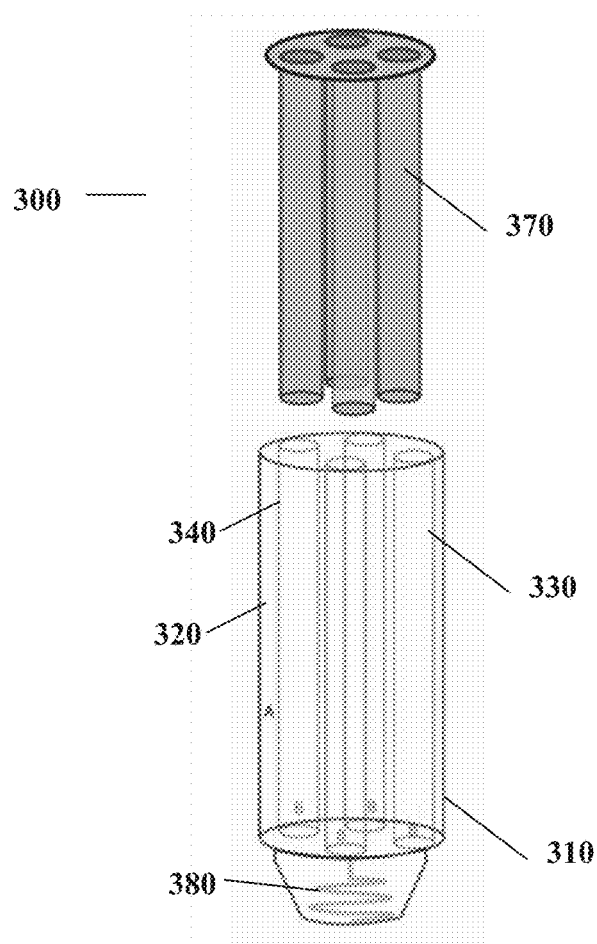
FIG. 19 includes schematic depictions and a photograph of delivery systems according to certain embodiments of the invention.
Figure 20:
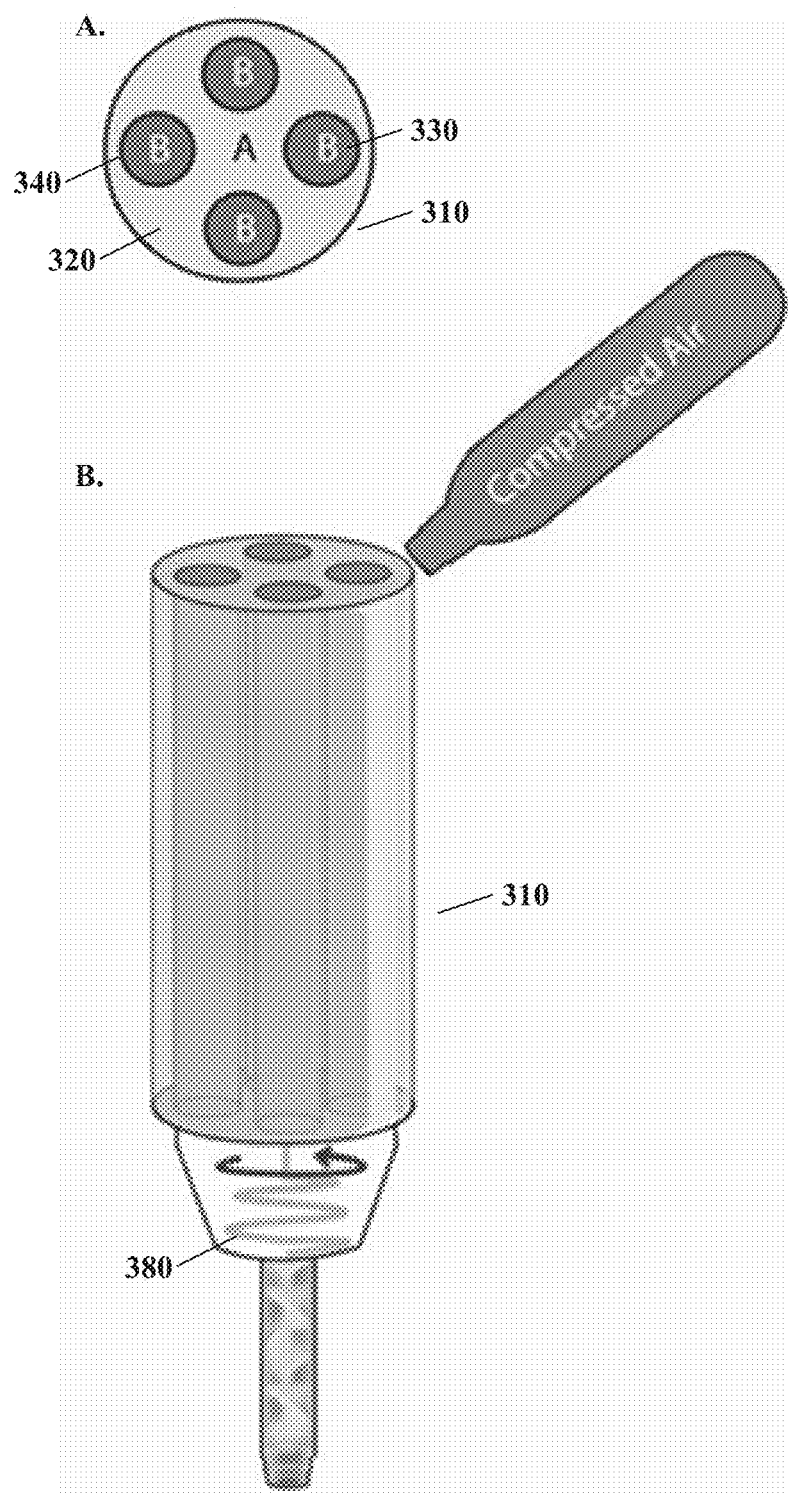
FIGS. 20A-B include schematic depictions and a photograph of delivery systems according to certain embodiments of the invention.

In the embodiment shown in FIG. 16, the cartridge containing the polyol would be detached in the system, an aeration mesh would be contained inside the cartridge and attached to a pull cord. Pulling the cord (similar to a rip cord on a lawnmower) would turn the aeration mesh inside the cartridge and entrain the head of air that is within the cartridge (as depicted in FIG. 16, step 2). The deployment mechanism into the body is shown as a ratchet mechanism but can consist of any of the above mentioned deployment mechanisms.

Portable Compressed Gas

While the embodiments described above have emphasized mechanical means for expelling fluid from dual barrel cartridges, other means, such as hydraulic or pneumatic means, can be used. In some embodiments, a portable compressed air cylinder 290 is used to effectuate gas entrainment and/or dispense fluid from the dual-barrel cartridge. For example, a portable air cylinder can be used to compress a piston, which urges fluids from one or more barrels of a cartridge, which fluids are then mixed by an impeller mechanism. The pressure generated from the compressed air expels a mixed, gas entrained formulation from the device and dispenses it into a site of interest on or within a patient. The impeller mechanism can be static (flow driven) or dynamic (driven by a motor or other driving means, including without limitation pneumatically by the same compressed air cylinder 290 or a different gas source 291). Compressed-gas driven devices according to the invention may have a number of advantageous characteristics, including, without limitation:

Ease of use (press a button to trigger release)

Ability to expel more viscous liquids because of use of higher pressures

Ability to modulate to complete dispense in a preset time

In devices according to embodiments of the invention, compressed gas may be provided by means of pre-pressurized gas cylinders, or in the alternative, a chemical reaction may generate gas within a chamber such as a cylinder to minimize the danger inherent in transporting pressurized canisters, particularly in remote and dangerous areas such as battlefields. In preferred embodiments, the chemicals that react to generate the gas will remain inert until their reaction is triggered by a user, at which point they will rapidly react to generate a volume of gas sufficient to drive successful deployment of foam within a patient. Any suitable gas generating chemistry may be used in accordance with the invention, including without limitation a sodium azide ($NaN_3$) and potassium nitrate ($KNO_3$) reaction. Chemical gas sources also permit delivery systems to be packaged in relatively small pieces for compact storage and portability, then assembled prior to use. For example, the nozzle and compressed air cylinder can be screwed onto to the handle prior to use. Various compressed gas-driven configurations of the delivery system are shown in FIGS. 17-20.

Compressed Gas and Bladder Canister Design

In an exemplary embodiment, compressed gas is released and pushes on a plunger that advances within one or more barrels of a multi-barrel fluid chamber in which one or more components of an in situ foaming formulation are contained in separate bladders. The plunger, when advanced, pierces the component bladders and forces the components through a dynamic mixing section and/or a static mixing section before the mixture is expelled from the device and on or into the body of a patient. In use, the device is engaged as follows: The handle is squeezed in order to break the seals of the CO2 chamber. Simultaneously the multiple bladders that contain components A&B are pierced by a series of sharp cones. The cones also act as a bulk stage mixing path for components A&B. Components A&B merge and are forced into the central tube. Located inside the central dispensing tube is a dynamic mixing turbine. The bulk mix of A&B is forced through to the distal tip which contains a final short phase of static mixer. The mixed components are finally dispensed into the body through an outlet While the disclosure above has generally dealt with multi-barrel chambers for in situ forming foam delivery systems, it will be understood that the reactive components for forming foams can be separated by a variety of means, which may be fixed and permanent or, alternatively, temporary and removable. In certain embodiments, a delivery system 300 of the invention includes a chamber 310 containing separate fluid components 320, 330 of an in situ foaming formulation which are, initially, separated by one or more films 340 which are capable of being ruptured by a rupturing mechanism 350. The device 300 includes a hand crank 360 attached, directly or indirectly, to a crank shaft 361 for advancing a plunger 370 forward, thereby bringing the film or films 340 in contact with the rupturing mechanism and expelling the material fluid components 320, 330. An impeller 380 is attached to the crank shaft 361 and, as the hand crank 360 is rotated, the impeller 380 turns and mixes the fluid components 320, 330. A reducing gear 362 can be interposed between the hand crank 360 and the crank shaft 361 to reduce the numbers of turns of the hand crank 360 required to expel the fluid components 320, 330 and/or to decrease the torque needed to turn the hand crank and mix fluid components 320, 330 which have high viscosity, or which form a high viscosity mixture.

Figure 23:
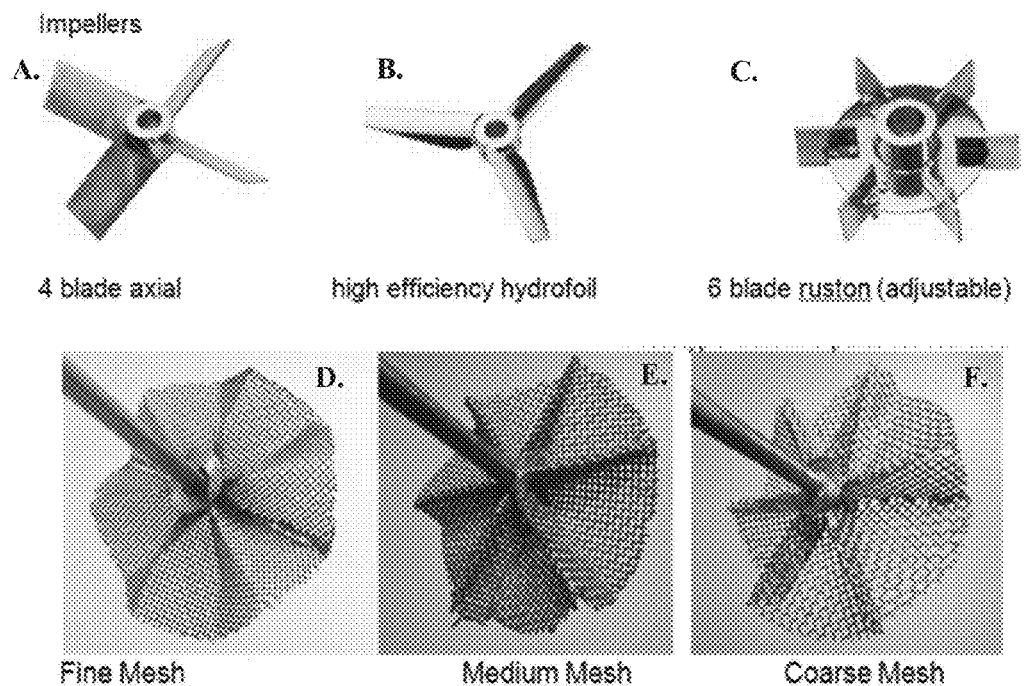
FIGS. 23A-F include views of exemplary impellers compatible with certain embodiments of the invention.
Figure 24:
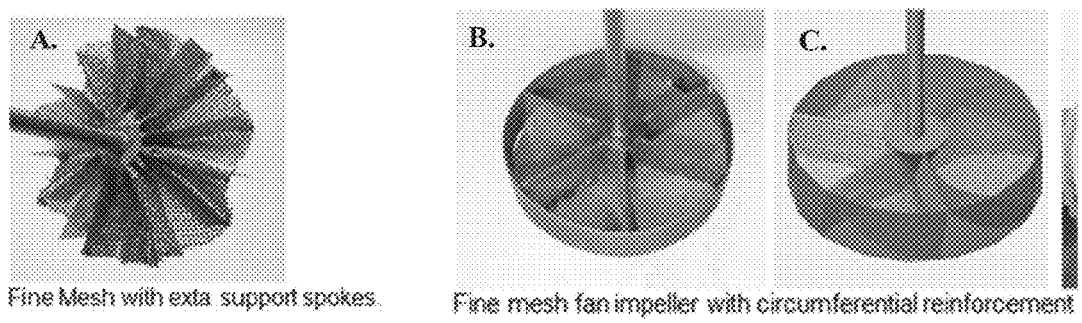
FIGS. 24A-C include views of exemplary impellers compatible with certain embodiments of the invention.

Devices according to this embodiment have several advantageous characteristics, including without limitation (i) Hand operation such as a lever or twisting motion could ease deployment because of mechanical leverage; A winding spring mechanism can be used to generate force needed to dispense the material and allow the medic to press a release button to deploy the material into the body; (iii) A battery driven shaft could also be incorporated into the delivery system. (iv) Reducing gears can be used to get a 16:1 "turn to dispense" ratio. Potentially you can mix and expel the material at the same time or using a single type of motion; (v) The mixing impeller(s) are can provide very efficient mixing and does not require high pressures such as with the static mixing nozzles; (vi) The impellers may release dissolved gases to create the required nucleation sites for foaming; (vii) Coaxial placement of part A and B in the cartridge to reduce overall volume. Exemplary reducing gears and impellers are shown in FIGS. 21, 22, and 23.

Alternate Mixing Concepts: Mixer Plate Mixing Element

Figure 25:
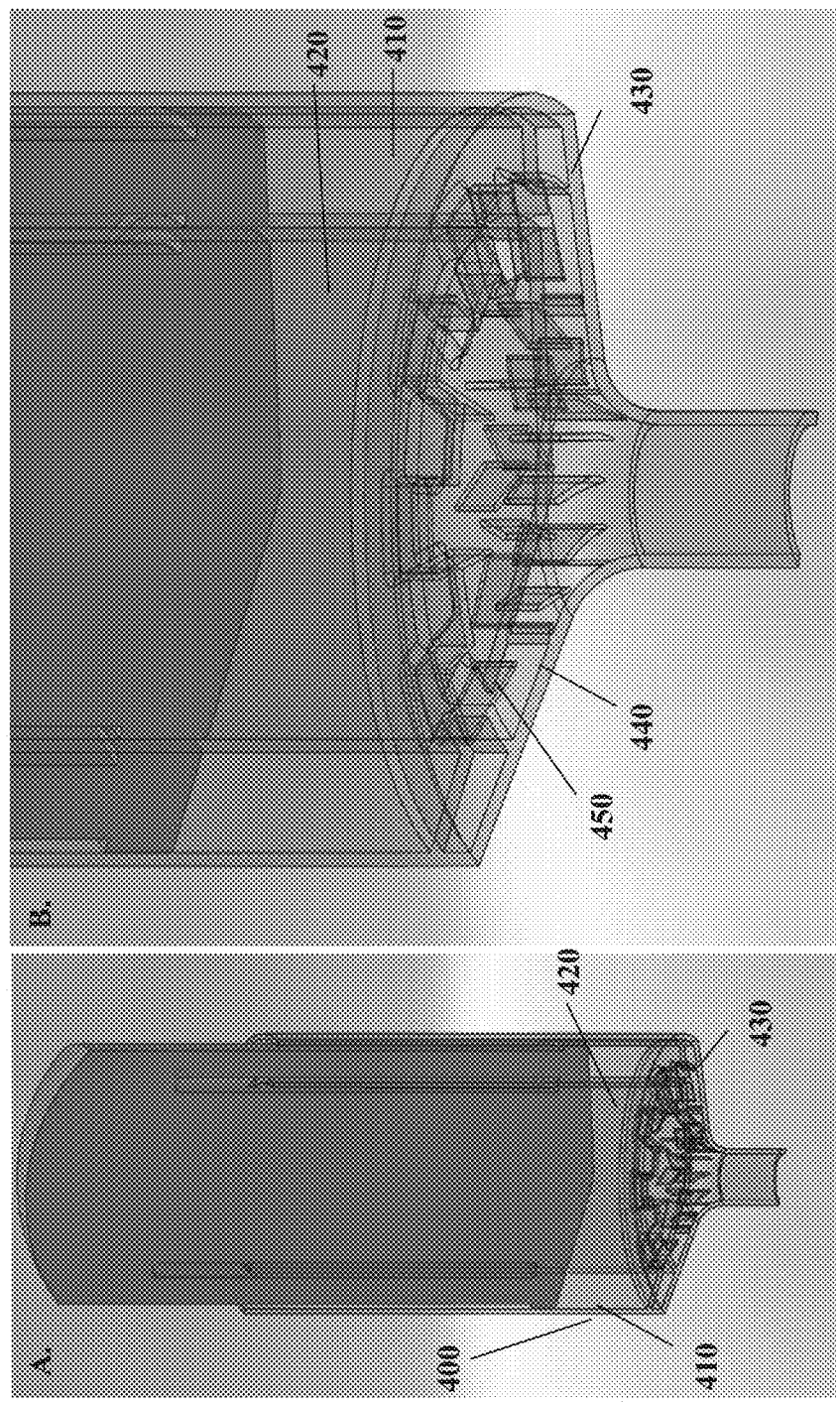
FIGS. 25A-B include schematic depictions of an exemplary chamber with concentric fluid subchambers according to certain embodiments of the invention.
Figure 26:
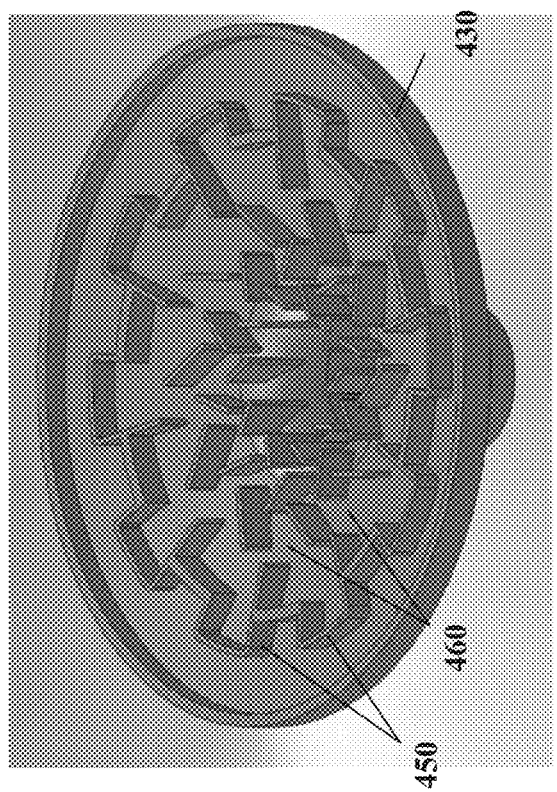
FIG. 26 includes schematic depictions of an exemplary distal chamber surface and an exemplary concentric mixing plate arrangement according to certain embodiments of the invention.
Figure 27:
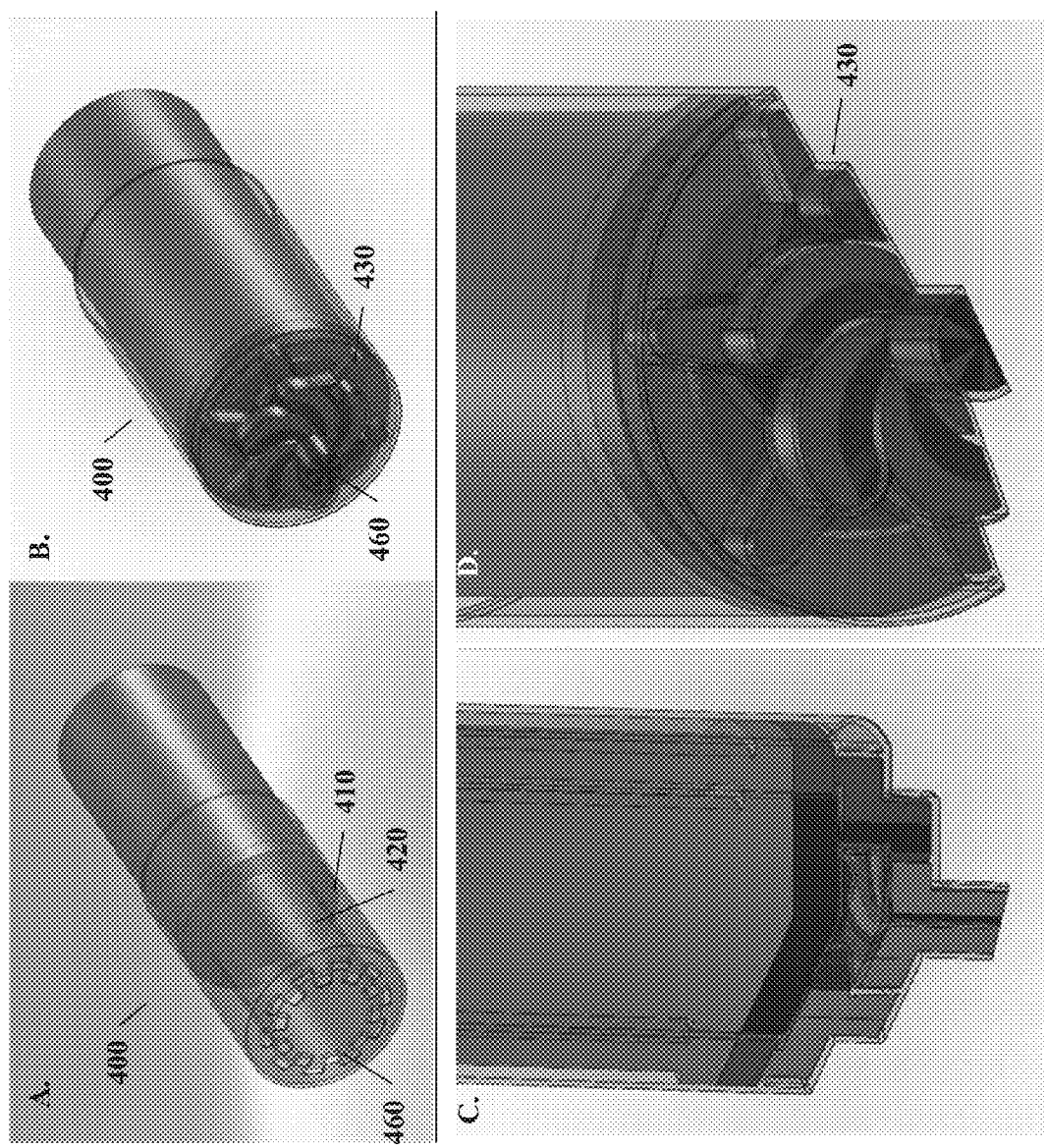
FIGS. 27A-D include depictions of fluid sub-chambers according to embodiments of the invention FIG. 28 includes depictions of mixing plates according to certain embodiments of the invention.

In certain embodiments of the invention, the mixing of fluid components is achieved using mixing areas characterized by a relatively large surface areas (as opposed to the relatively small surface area of a standard static mixer) to reduce the back pressure required for uniform mixing. In preferred embodiments, a fluid chamber 400 contains fluid components are arranged in concentric subchambers 410, 420 sealed at their distal ends (i.e. the ends nearest the outlet of the delivery system) with a plastic membrane. The membrane seal is broken by pressure which can be a user-operated actuator action such as a squeeze or push of the grey part shown in FIG. 25. In some embodiments, a check valve or a one way valve is utilized rather than a puncturable plastic membrane; the valve opens upon the application of pressure. The two components are mixed by pushing the liquid phases into the convoluted paths of the large mixing area 430 at the distal end of the container (FIG. 26). The distal end of the chamber 400 optionally includes walls 450 extending away from the main surface of the chamber at an angle such as 90 degrees to define a series of passageways 460 that repeat from the outer circumference to the inner circumference of the distal end of the chamber, as shown in FIG. 26. A series of color images shows two liquid parts (shown in red and green of FIG. 27) moving through the convoluted pathway and mixing and/or folding into each other.

Figure 28:
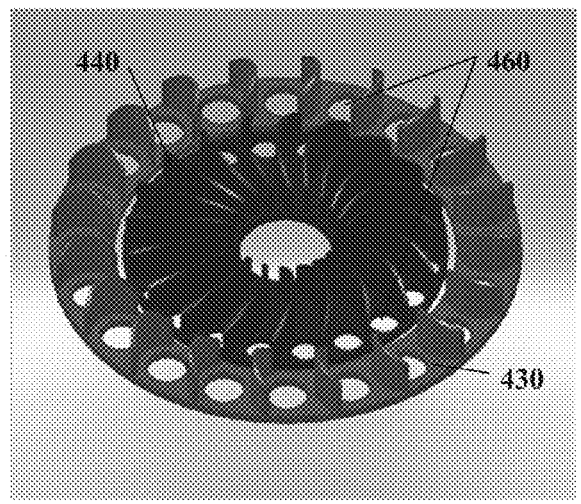
Figure 29:
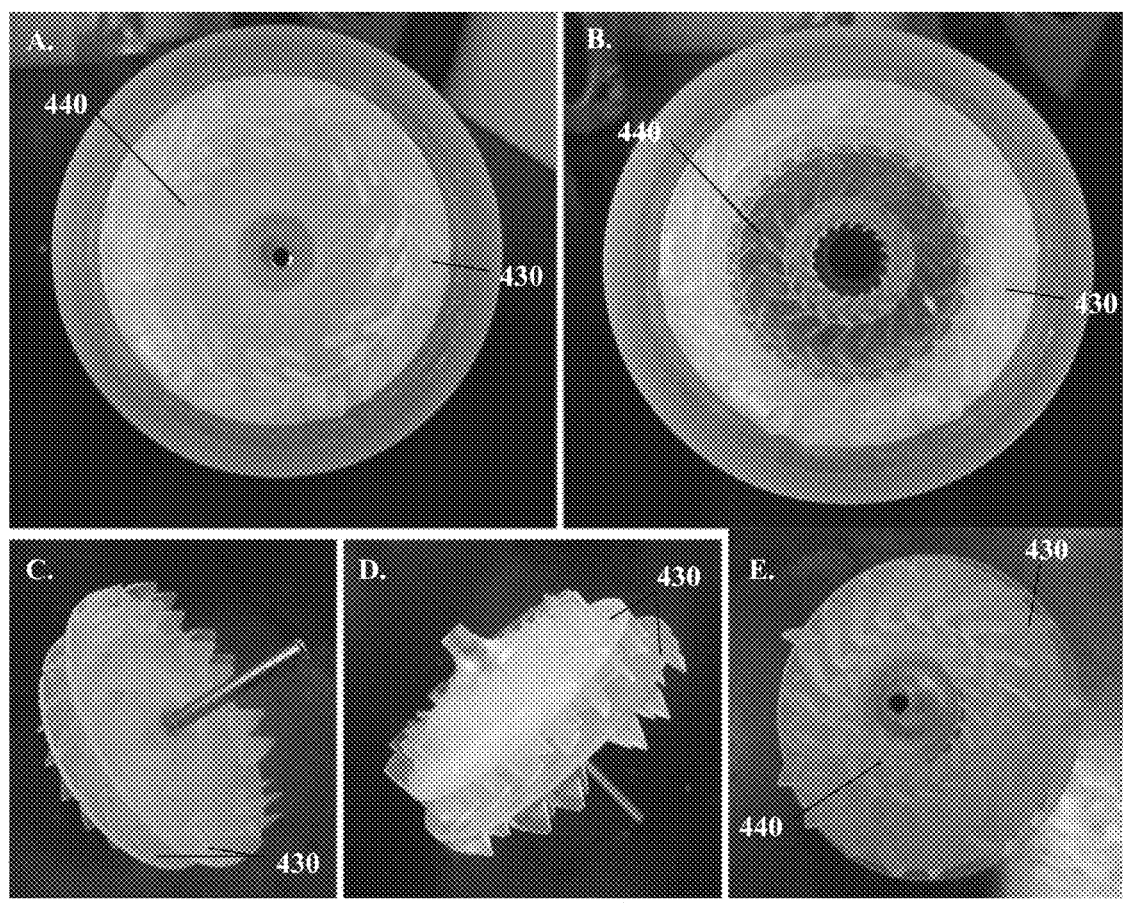
FIGS. 29A-E include photographs of prototype mixing plates according to certain embodiments of the invention.

In a preferred embodiment, the mixing area comprises two concentric plates with an outer mixing plate 430 rotating in a first direction and an inner mixing plate 440 rotating in a second direction. FIG. 28. Each of the mixing plates optionally includes a plurality of apertures 460 to permit fluid to flow or move through each mixing plate. Exemplary mixing plate and chamber arrangements are shown in FIGS. 28-29.

Alternate Canister Designs

Figure 30:
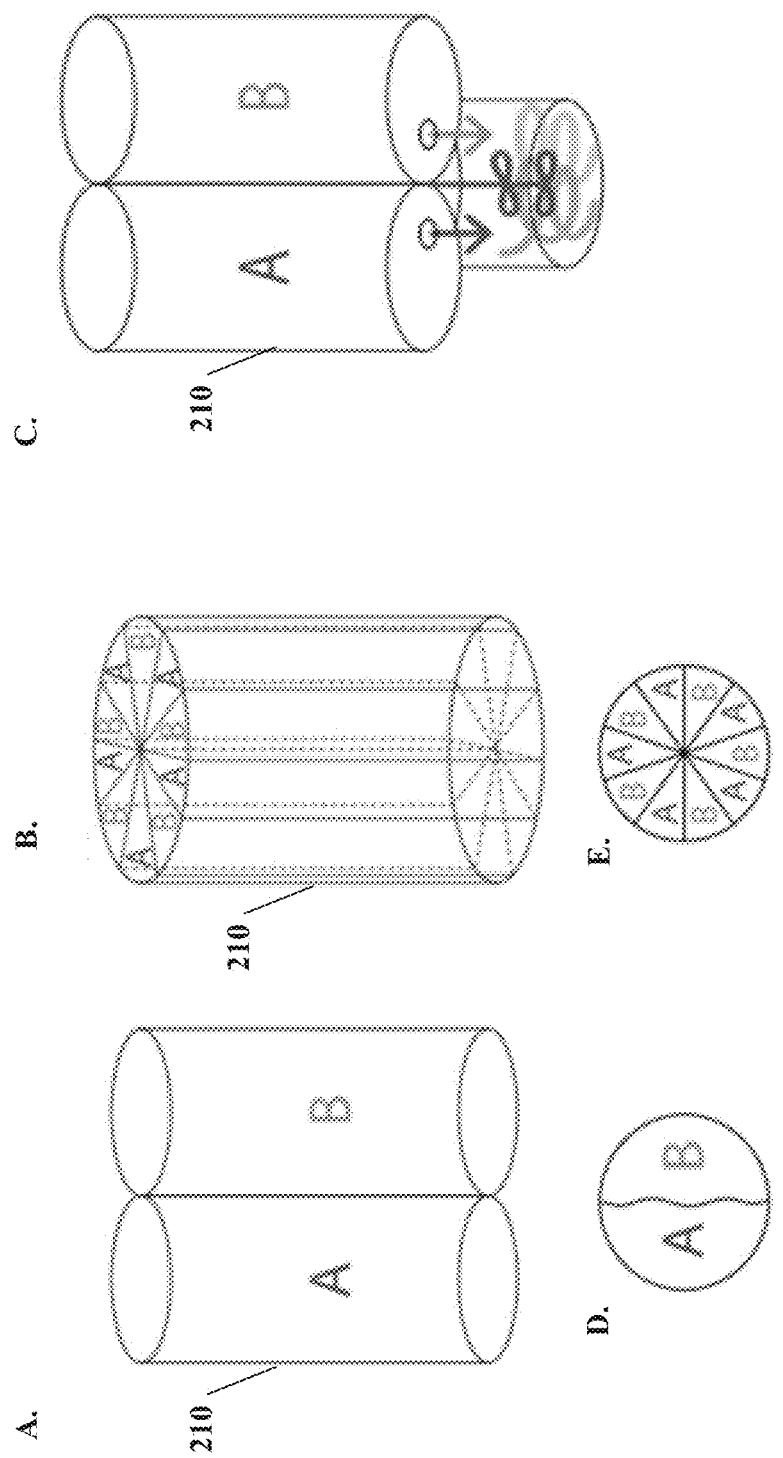
FIGS. 30A-E include schematic depictions of exemplary fluid canisters and iris mixing arrangements for delivery systems according to certain embodiments of the invention.

In this concept the suggested layout of the canister can help with efficient mixing of parts A and B and combined with an impeller would provide a reproducible mixing method for polymers eliminating the need for mixing nozzles (FIG. 30).

Figure 31:
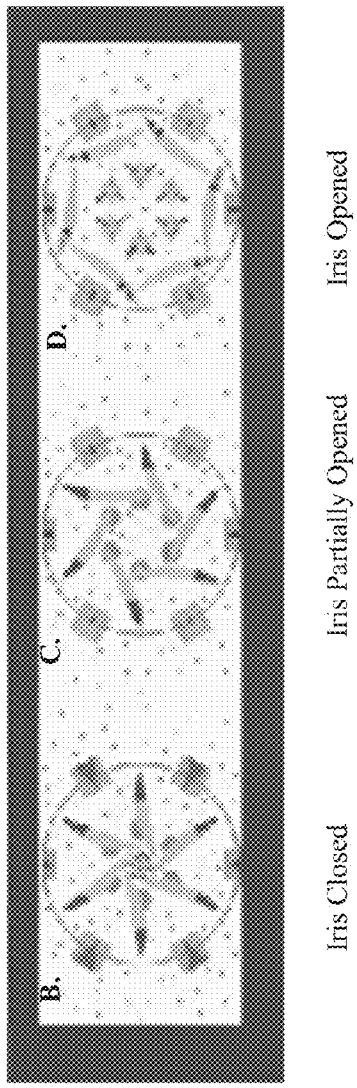
FIGS. 31A-D include schematic depictions of exemplary iris mixing arrangements for delivery systems FIGS. 32A-C include pictures of exemplary spring-loaded cutting needles according to certain embodiments of the invention.

In another embodiment, rather than utilizing a crushable or rupturable membrane, an iris mechanism is used to keep components A and B separate until ready for use. The iris mechanism separates each component A, B into its own respective compartment, and as the iris mechanism is opened parts A and B are brought into fluid contact with one another. The iris mechanism can also be used to mix parts A and B by opening and closing the iris several times, e.g. via a quick turn/twist with the hands prior to dispensing into the body. Images of this concept are shown below (FIG. 31):

Alternate Site Insertion Method (Cutting Needle)

Figure 32:
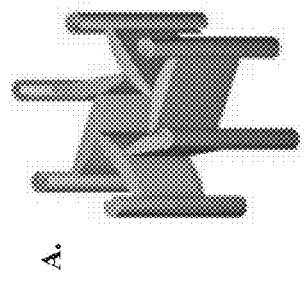
Figure 32:
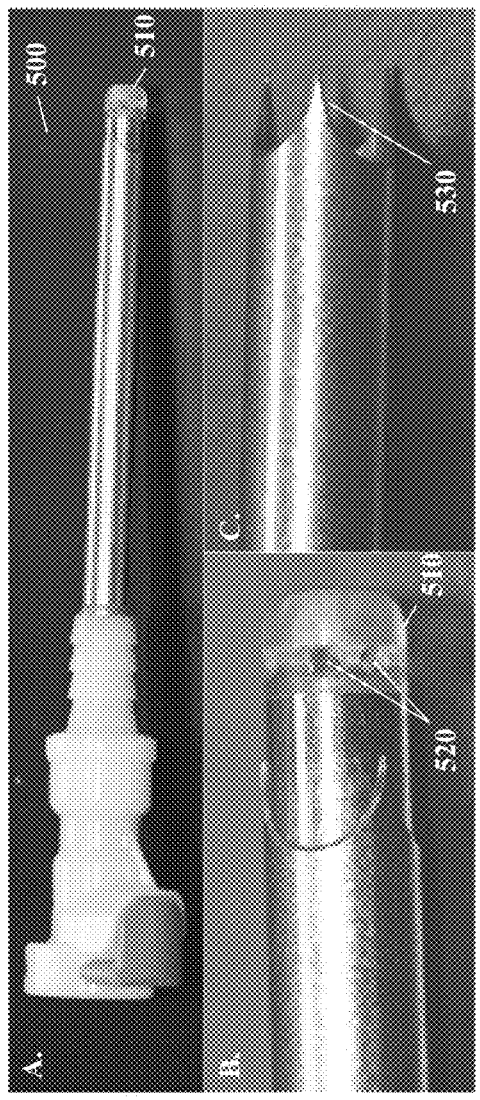

The distal tip of the delivery system, in certain embodiments, includes a spring-actuated cutting needle 500 that can be used to access closed body cavities such as the abdominal cavity in which foam deployment is desired. In preferred embodiments, such as the embodiment shown in FIG. 32, the distal tip includes a blunt end 510 comprising one or more apertures 520 for the expulsion of in situ forming formulations. A spring-actuated cutting needle 530 is disposed, at rest, at a fixed distance from the blunt end such that, when the tip is pressed into the skin of a patient, the cutting needle advances relative to the blunt end, thereby exposing the cutting needle so that the skin and any tissue layers overlying the body cavity in which in situ forming foam deployment is desired can be penetrated.

Motorized Mixer with Compressed Gas Dispenser

In animal studies, the inventors have used a motorized mixer in conjunction with compressed gas to mix and dispense the liquid phases. This system can be miniaturized and adapted for battlefield use. According to certain embodiments of the invention, compressed $CO_2$ cylinders are used to power both the motor and the piston, though in some embodiments, compressed gas is provided by a chemical reaction as discussed above.

Figure 33:
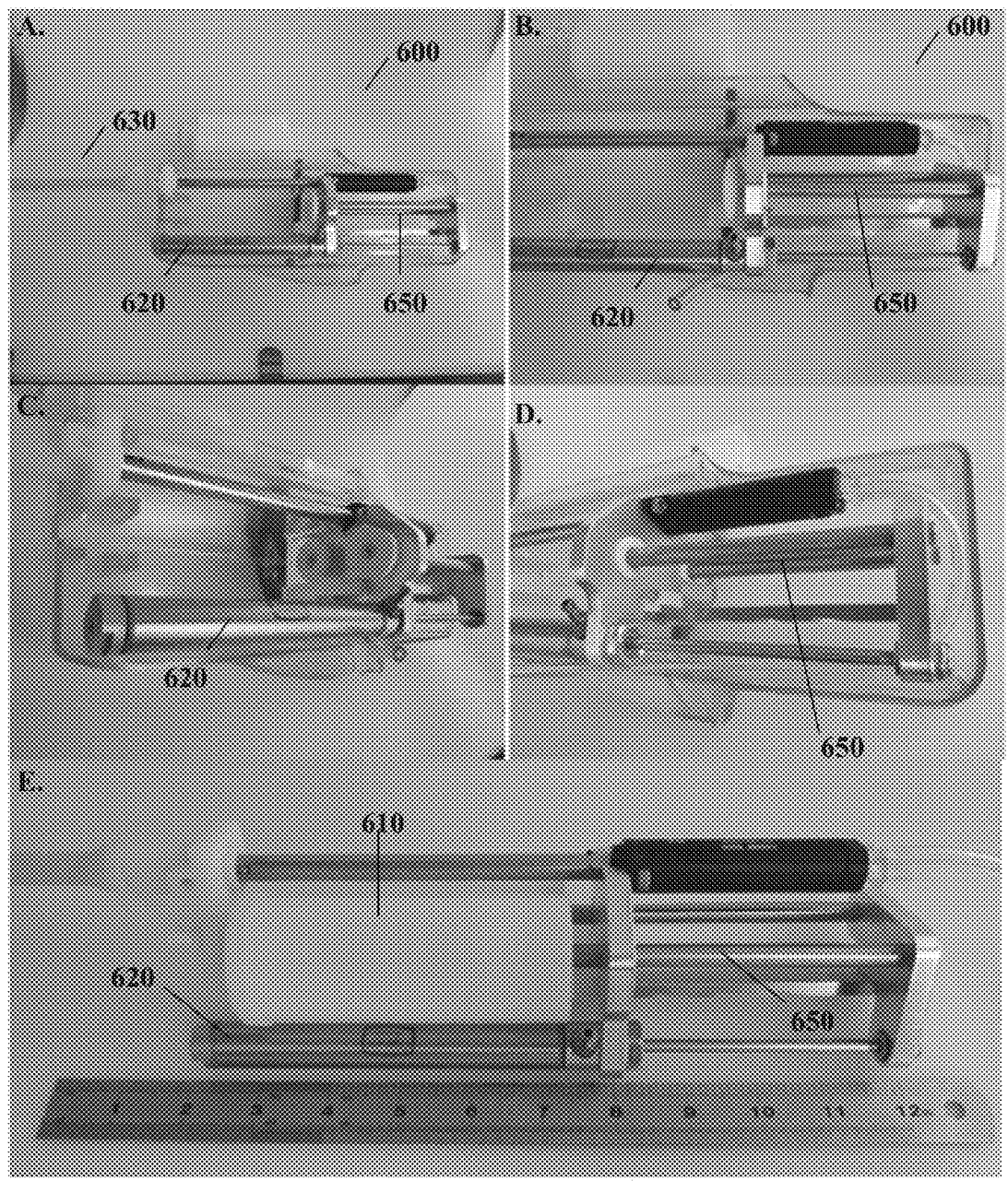
FIGS. 33A-E include pictures of exemplary delivery systems with motorized mixers according to certain embodiments of the invention.

In one example, the following components are used:
Motor: Micro Motors Inc. Santa Ana, Calif.
Model #MMR0014, RPM 1750 @ 90 psi, Tachometer reading 1500 RPM at 80 psi.
Stall Torque 110 inch ounces.
Piston: Bimba
Model #SR-044-D, max pressure 100 psi, ¾" diameter, 4" length.
Dimensions of overall system with nozzle folded: 12×8×6 inches Images of the design are shown in FIG. 33 (gas cylinders are not pictured).

Figure 34:
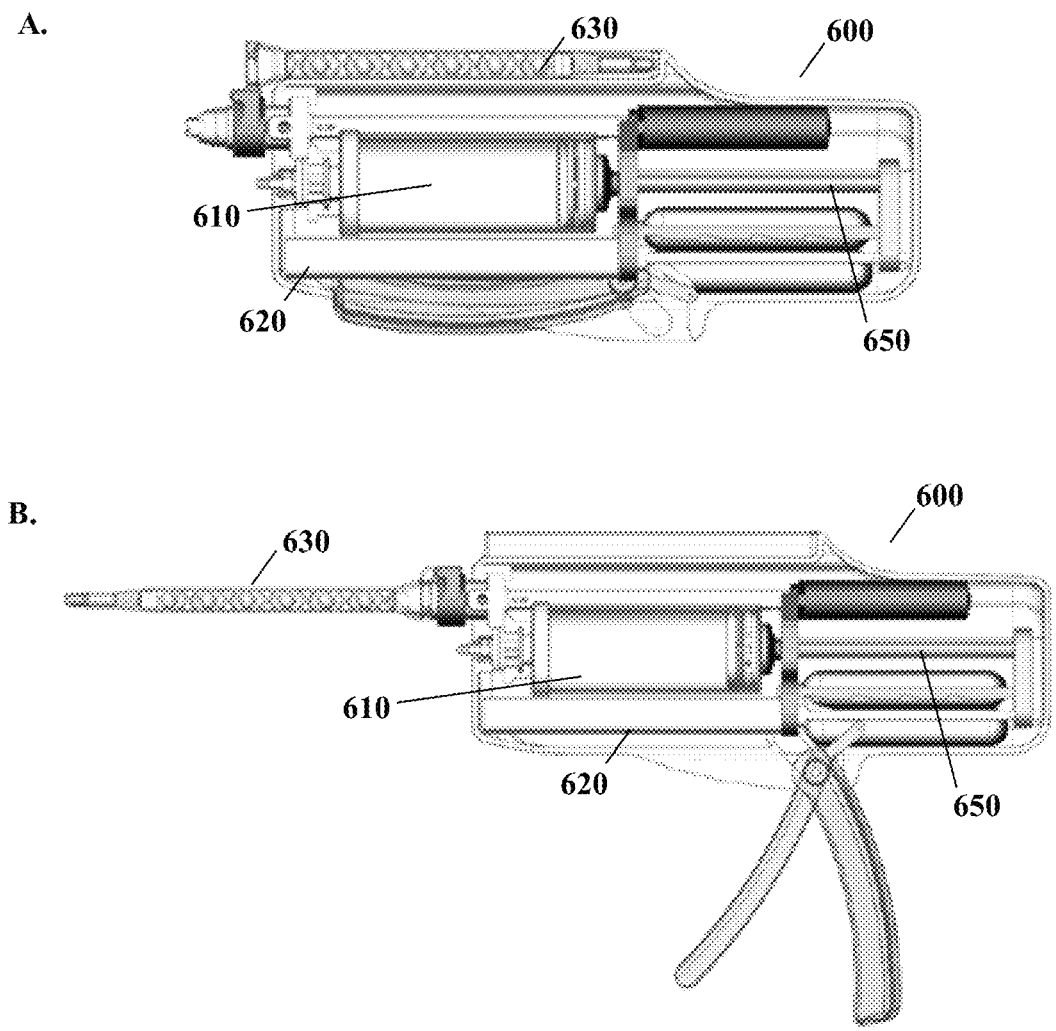
FIGS. 34A-B include schematic depictions of exemplary delivery systems with motorized mixers according to certain embodiments of the invention.

CAD images of the system are shown in FIG. 34. In both embodiments, the device 600 includes one or more fluid chambers 610 as discussed above, as well as a motorized actuator 620, a mixing nozzle 630, and pistons 650 that are advanced by the motorized actuator 620 to compress the fluid chambers 610, thereby evacuating the in situ foaming formulation through the mixing nozzle 630 and into the body of the patient. Aeration and/or mixing are aided by the motorized mixer assembly 660, which connects to the mixing nozzle 630.

Connection Between the Device and the Dispensing Tip

Figure 35:
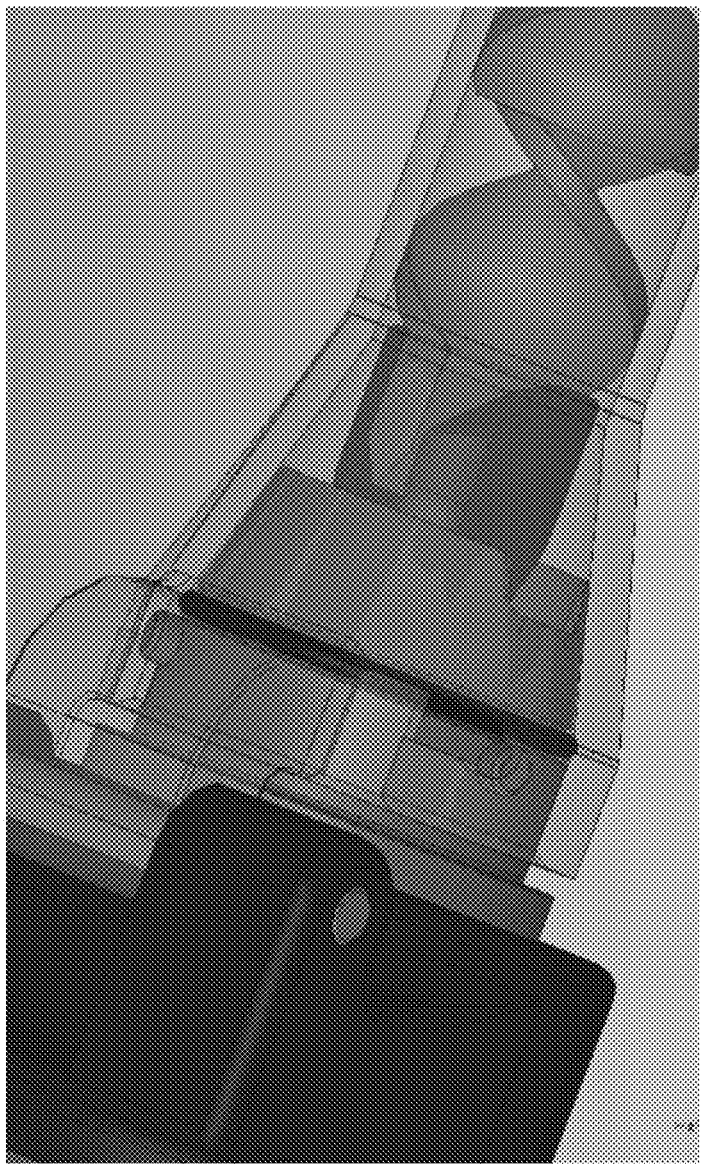
FIG. 35 includes a schematic depiction of an exemplary connector for engaging a mixing tip with a motorized mixer according to certain embodiments of the invention.

In some embodiments, the mixing tip 630 of the device is connected to the motorized mixer 660 as shown in FIG. 35. The connection between the dispensing tip 630 and the motorized mixer advantageously does not require alignment of the mixing element 631 and drive shaft 661. Mixing elements 632 are held in between the recesses 662 in the drive shaft 661. The drive shaft 661 is contoured, spring loaded and rotates to accept the mixing elements at any angle. The nut 633 twists and locks in position. An o-ring provides a seal for the polyol and isocyanate.

Multi-Prong Delivery Catheter

Figure 36:
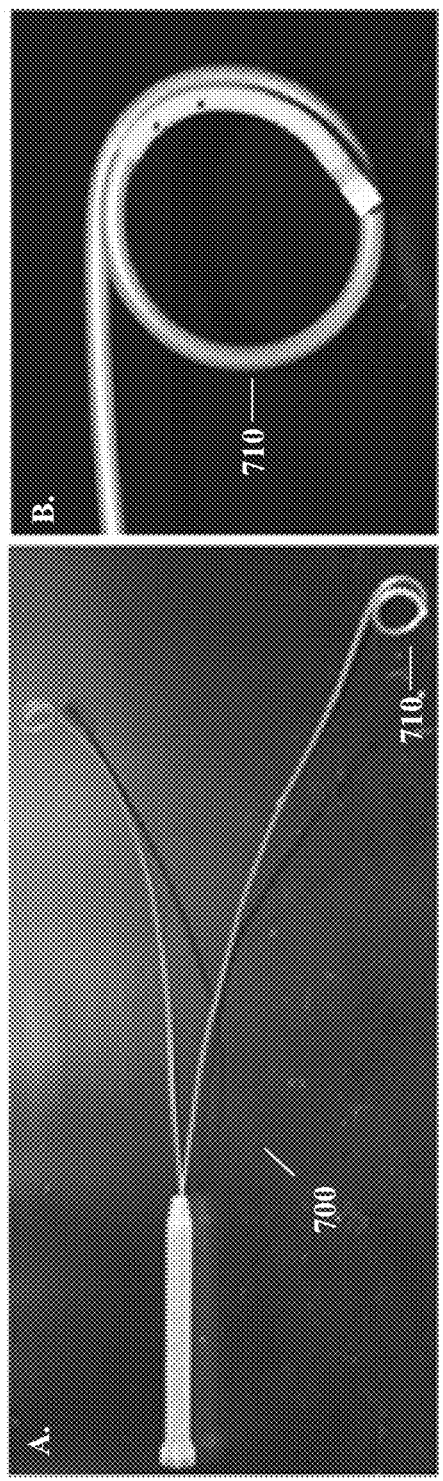
FIGS. 36A-B include photographs of exemplary multi-prong delivery catheter tips according to certain embodiments of the invention.

In some embodiments, dispersion of air-entrained in situ forming formulations within closed cavities is improved by the use of multi-nozzle dispersal tips. In some embodiments, a multi-nozzle dispersal tip includes a plurality of catheters having multiple apertures for discharging fluids into a body cavity. FIG. 36 depicts a first exemplary multi-prong tip 700 (Prototype #1). The catheters are reinforced with flat stainless steel braids and over extruded with a Pebax layer. The end of each catheter optionally includes a pig tail curve 710 so that the catheter is atraumatic during insertion. The exemplary multi-prong tip 700 shown in FIG. 36 advantageously deposits material on both sides of the spine when used in the abdominal cavity, thereby allowing the foam to reach the vena cava and aorta. However, small diameter catheters may have difficulty tracking to the sites of abdominal gutters.

Figure 37:
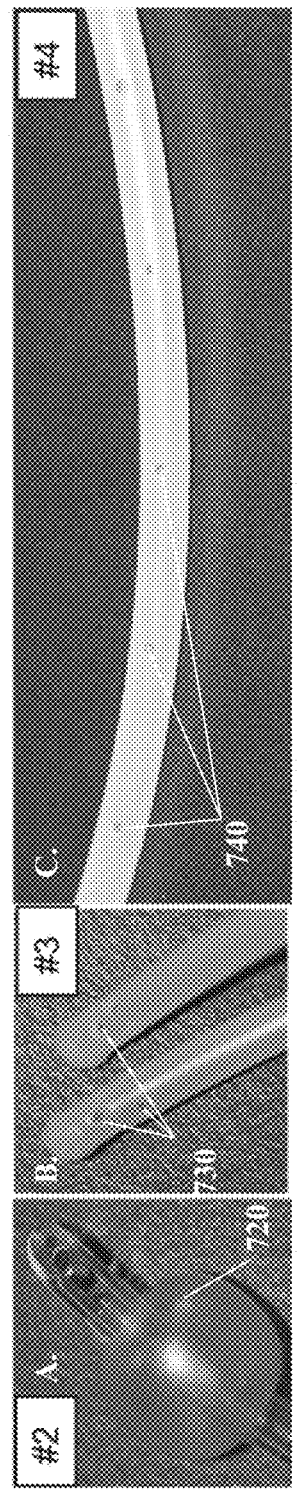
FIGS. 37A-C include photographs of exemplary delivery catheter tips according to certain embodiments of the invention.

Prototypes 2-4 (shown in FIG. 37A-C) have larger diameters, improving their ability to track to gutters of the abdomen.

Prototype #2 has a 5 mmID×8 mmOD tube with end hole and includes a balloon 720 to help keep the tip in position. Prototype #3 includes a 4 mmID×7 mmOD tube with 8 radially distributed end holes 730. The catheters of prototype #3 are made of nylon and are stiffer than prototype 2.

Prototype #4 also includes a 4 mmID×7 mmOD nylon tube but has 24 holes 740 along the length of the tube.

Lock Out Mechanism

Figure 38:
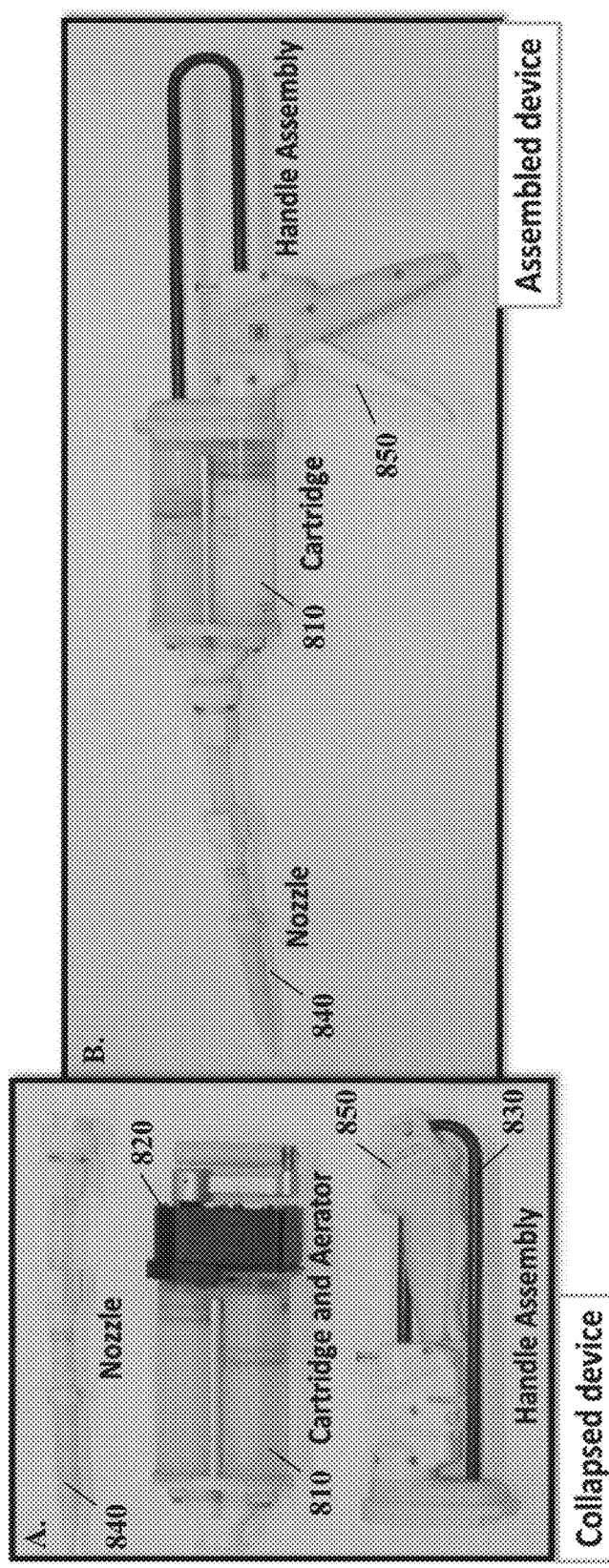
FIGS. 38A-B include photographs of assembled and collapsed delivery systems according to certain embodiments of the invention.
Figure 39:
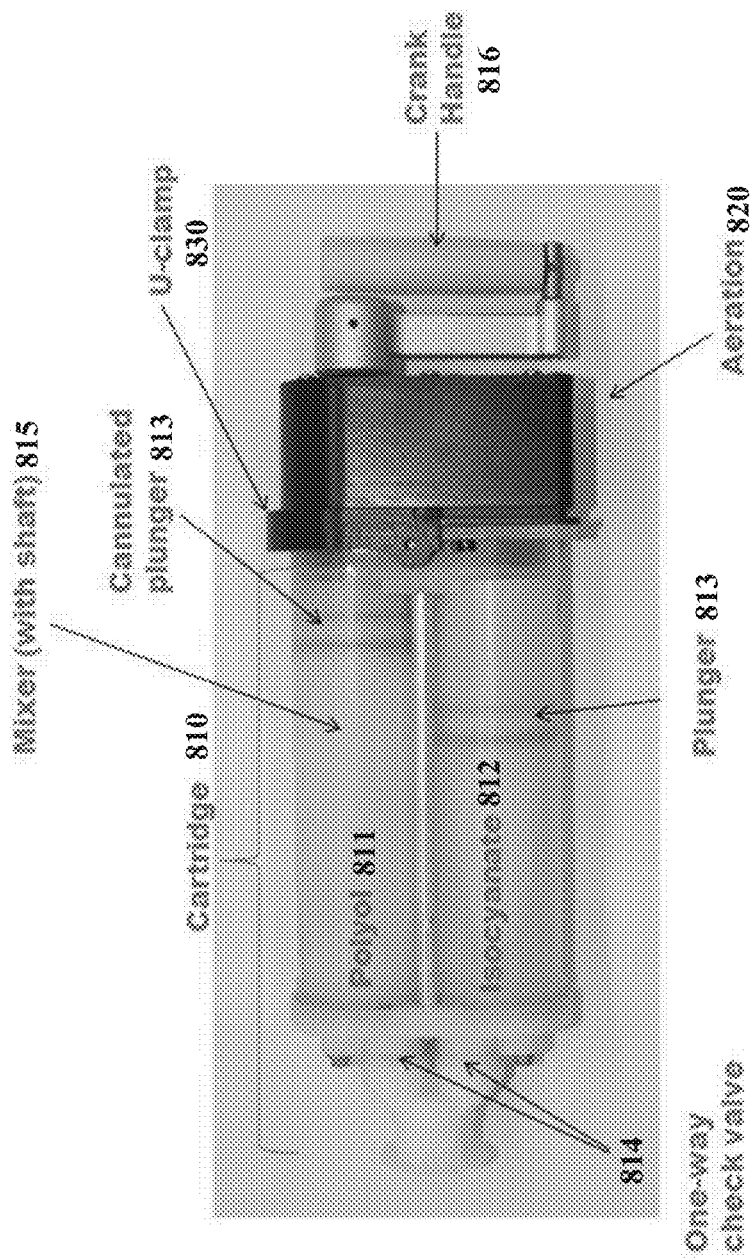
FIG. 39 includes a photograph of a cartridge including a lockout mechanism.
Figure 40:
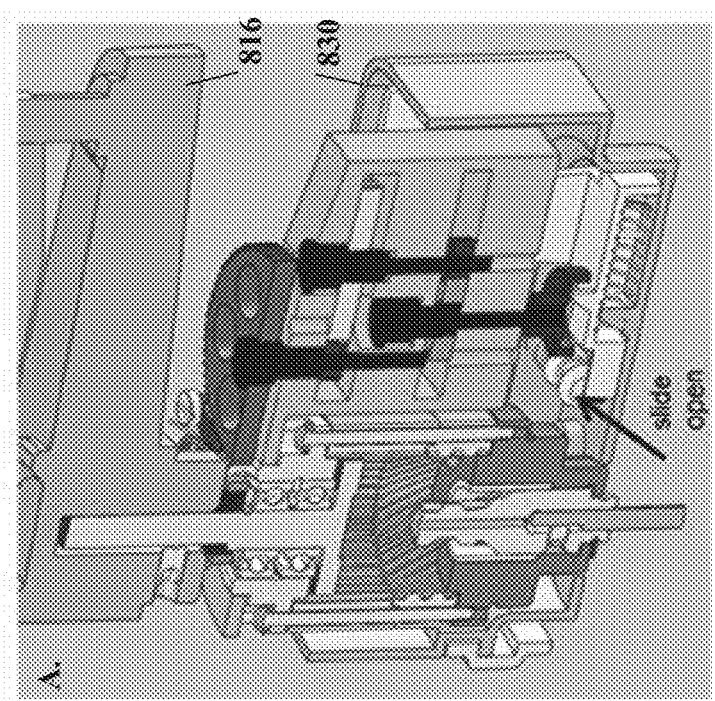
FIGS. 40A-B include schematic cross-sectional depictions of a lockout mechanism in the open and locked positions according to certain embodiments of the invention.
Figure 40:
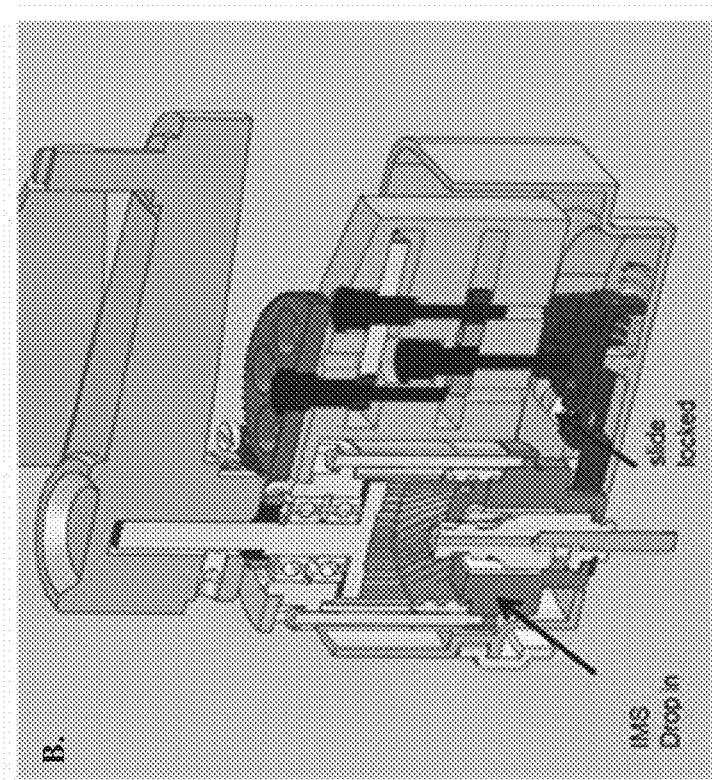

Formulations that are not fully aerated may not efficiently promote hemostasis, it is desirable in some instances to prevent the delivery of unaerated or partially aerated formulations delivered using delivery systems of the invention. Thus, in preferred embodiments, the delivery system includes a lockout mechanism to prevent the deployment of formulations until aeration is complete. As shown in FIGS. 38A and 39, in an exemplary embodiment of the invention, a delivery system 800 is provided to users in multiple pieces including a nozzle 840 and an actuator 850, along with a cartridge 810 and an aerator 820 which are provided as a single unit held together with a u-clamp 830. The cartridge includes at least two chambers 811, 812 which contain and separate the isocyanate and polyols components of the foaming formulation. Each chamber 811, 812 includes a plunger 813 for evacuating the contents of the chamber, and each chamber also optionally includes a one-way valve 814 disposed opposite the plunger, to ensure that fluids that are evacuated from the chambers 811, 812 cannot be returned into the system 800. In addition, at least one of the chambers 811, 812 includes a mixer 815 such as the helical mesh and shaft arrangement described above; the plunger 813 in this chamber is cannulated to accommodate the shaft of the mixer 815. The shaft of the mixer, in turn, is connected (optionally via a reducing gear system as described above) to a hand-crank 816 or other mechanical actuator for aerating at least one of the fluid phases of the in situ foaming composition. The system 800 is initially provided to the user in a "locked" configuration such that the aerator and cartridge cannot be disconnected until certain user steps, including aeration, are completed. In one such arrangement, a user is required to aerate the foaming formulation by cranking a handle through a minimum number of turns before the device can be assembled to permit injection of the formulation into the body. In particular, the aerator 820 contains pins 821 that initially extend into the u-clamp 830. Once the threshold number of turns is reached, a spring mechanism pulls back the pins and allows the u-clamp to be removed and the aerator to be separated from the cartridge. At the same time, a ready indicator optionally changes status, (e.g. changes from black to white) to visually or audibly indicate to the user that aeration is complete. Once the cartridge is detached it can then be attached to the handle and deployed into the body.

Aerator Design with Ready indicator

Figure 41:
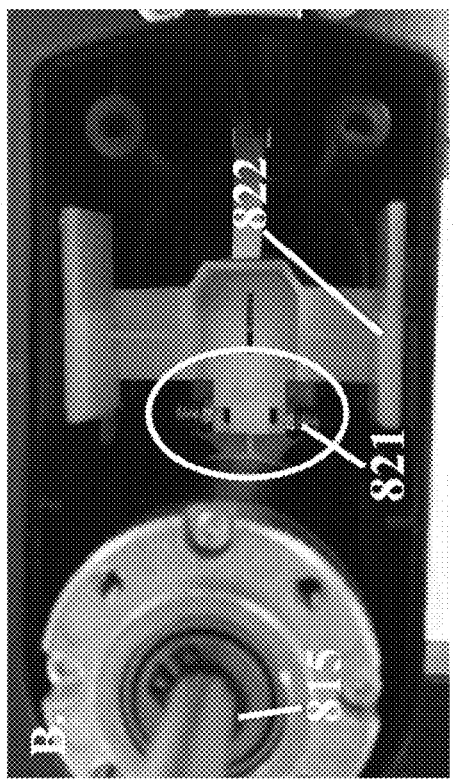
FIGS. 41A-B include photos of an exemplary lock-out and indicator mechanism.
Figure 41:
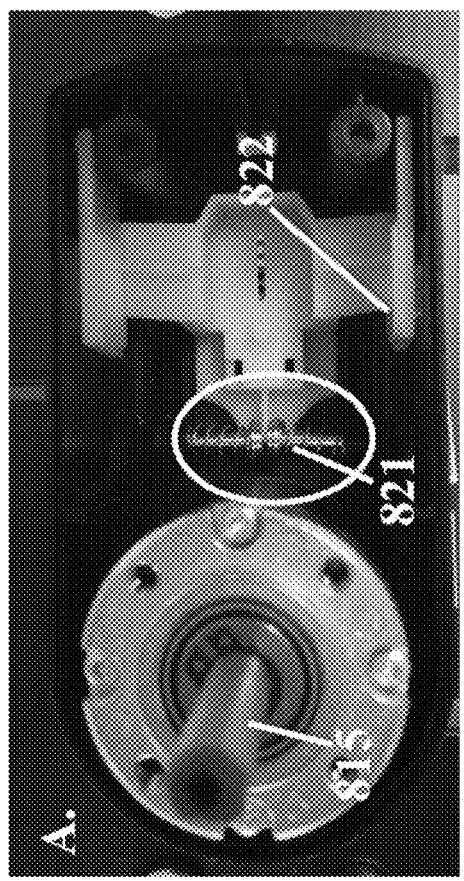
Figure 42:
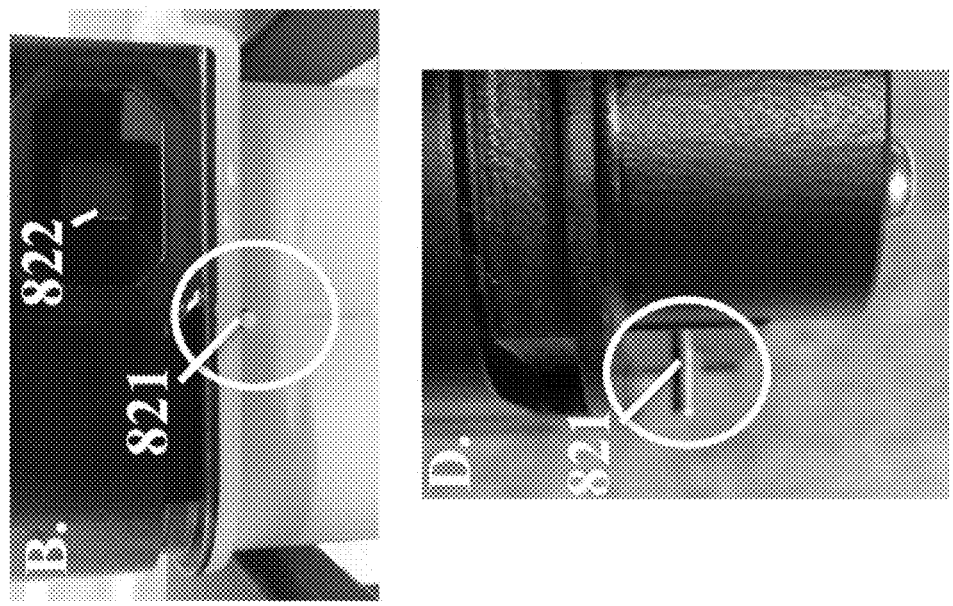
FIGS. 42A-D include photos of an exemplary lock-out and indicator mechanism.
Figure 42:
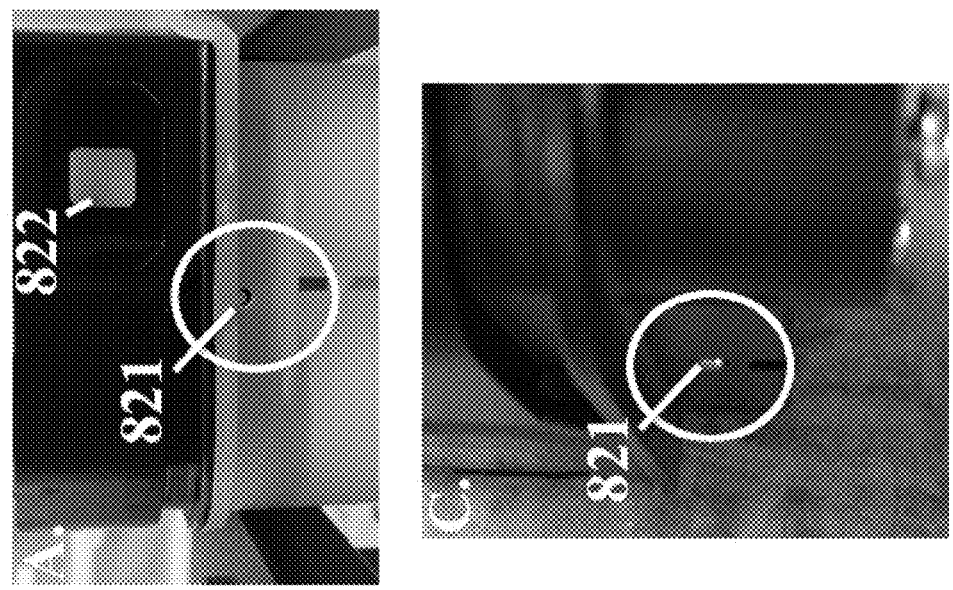

With respect to the aerator and the ready indicator, in an exemplary delivery system shown in FIGS. 41-42 the lockout mechanism and ready indicator form parts of an integrated system providing feedback to a user that the formulation is fully aerated and ready to be dispensed. In the pictured embodiment, at least one spring-loaded pin 821 (circled throughout the various views) is configured to reversibly mate with an indicator assembly 822. In a closed configuration, shown in FIGS. 41B and 42B and D, the indicator assembly 822 is in a "not-ready" state in which a portion of the assembly 822 is positioned so as to prevent retraction of the pin 821. After the impeller assembly 815 has moved through a pre-sent number of turns, however, the indicator assembly 822 is displaced so as to permit the pin or pins 821 to retract into the body of the cartridge, (shown in FIGS. 41A and 42A and C) permitting removal of the U-clamp and dispensing of the aerated formulation into the body.

Dose Slider

Figure 43:
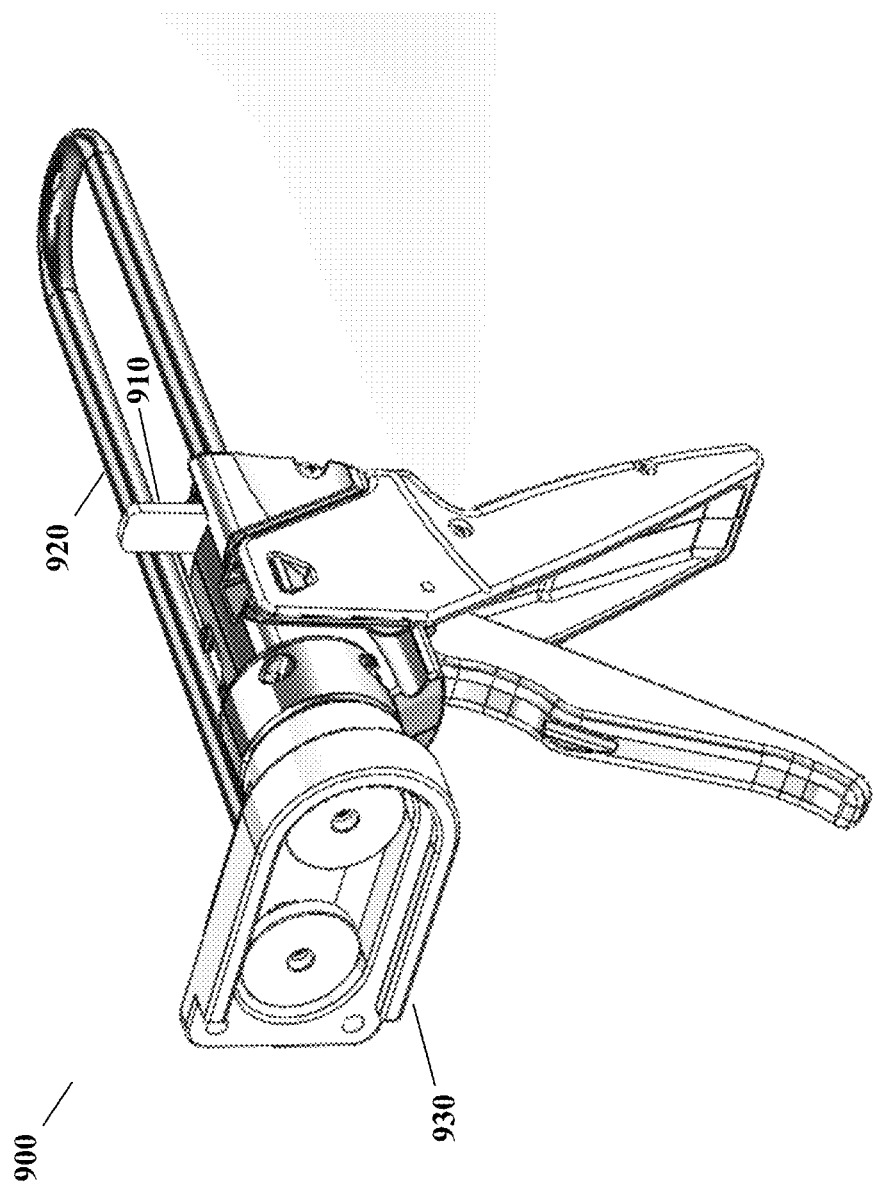
FIG. 43 includes a schematic perspective depiction of a handle assembly in accordance with embodiments of the invention.
Figure 44:
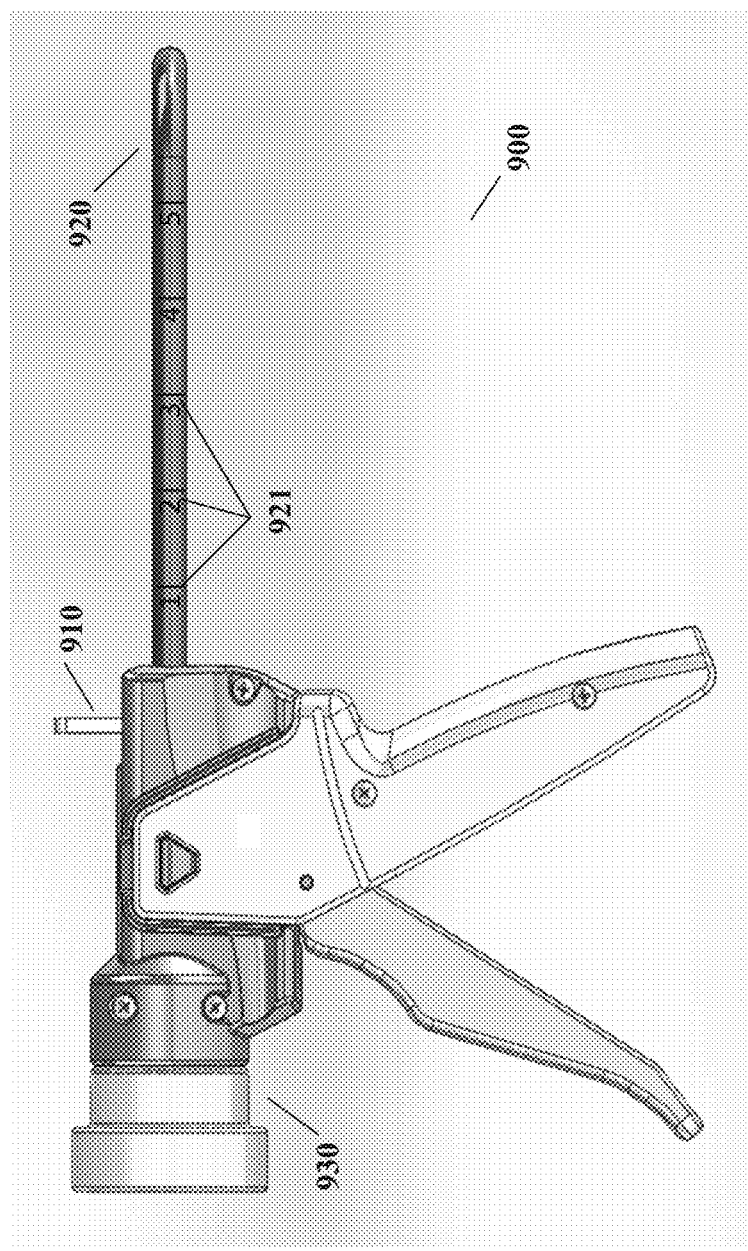
FIG. 44 includes a schematic perspective depiction of a handle assembly with a dose slider in accordance with embodiments of the invention.

It may also be desirable, in some instances, to tailor the quantity of foaming formulation delivered via a delivery system of the invention to a specific application or patient. For instance, an exemplary delivery system 900 includes a dose slider mechanism as shown in FIGS. 43-44, which permits a user to administer relatively less formulation to an individual in a lower weight or height percentile or to administer relatively more to an individual in a higher percentile. The dose slider 910 is an adjustable slide that is part of the handle assembly and which prevents the movement of the piston rods or pistons through their full range. In the embodiment shown in FIGS. 43-44, the dose slider is located on a piston rod 920 that is attached to the friction drive 930. The rod optionally includes markings 921 that indicate, either subjectively (e.g. small, medium and large) or objectively (e.g. volumetric indications) an amount of formulation that will be delivered. A user can move the slider 910 to a selected marking 921, thereby selecting the volume to be delivered. The slider 910 resides on the piston rods 920 behind the friction drive 930 and serves a positive stop for the friction drive 930. In particular, the slider prevents the friction drive from advancing forward and dispensing formulation.

While the examples presented above have focused on multi-component formulations for generating in-situ forming foams, those of skill in the art will appreciate that they can be adapted to function with single-part foaming formulations, and such adaptations are within the scope of the present invention.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Certain embodiments of the present invention have described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

The invention claimed is:

1. A medical device, comprising:
   a fluid cartridge comprising at least one chamber and at least one piston, wherein a volume of the chamber is determined by a position of the at least one piston;
   at least one impeller located within the at least one chamber;
   a static mixer in fluid communication with the chamber, the static mixer including a tip configured for insertion into a body of a patient;
   a first actuator adapted to move at least one of the impeller and the piston; and
   a lockout mechanism reversibly coupled to the fluid cartridge, wherein (a) the lockout mechanism is movable between a first configuration which prevents the movement of the at least one piston and a second configuration which permits the movement of the at least one piston and (b) the lockout mechanism moves from the first configuration to the second configuration after the impeller has undergone a predetermined number of rotations within the at least one chamber.

2. The medical device of claim 1, wherein moving the first actuator moves the piston, decreasing a volume of the chamber.

3. The medical device of claim 2, wherein the first actuator is one of a squeeze handle, a crank handle, a ratchet, or a piston pump.

4. The medical device of claim 1, wherein moving the first actuator aerates a fluid in at least one chamber of the cartridge.

5. The medical device of claim 4, wherein the first actuator is configured to reversibly couple to one or more of the at least one piston and the at least one impeller.

6. The medical device of claim 1, further comprising a cylinder loaded with compressed gas, wherein activation of the first actuator causes the evacuation of compressed gas from the cylinder and one of (a) the advancement of the piston within the at least one chamber, thereby expelling the contents of the fluid cartridge, or (b) the movement of the impeller within the at least one chamber, thereby aerating a fluid within the cartridge.

7. The medical device of claim 1, wherein the impeller comprises a mesh.

8. The medical device of claim 1, wherein a rim of the impeller contacts a wall of the chamber.

9. The medical device of claim 1, wherein the static mixer comprises a substantially cylindrical outer shell defining a lumen, the tip of the static mixer comprises a plurality of apertures through the shell, and a plurality of mixing elements are disposed within the lumen.

10. The medical device of claim 9, wherein the mixing elements are selected from the group consisting of X-grids, beads, and mesh.

11. The medical device of claim 1, further comprising a movable dose slider configured to stop the movement of the at least one piston beyond a position determined by a position of the movable dose slider.

* * * * *